US009994228B2

(12) United States Patent
Krueger

(10) Patent No.: US 9,994,228 B2
(45) Date of Patent: Jun. 12, 2018

(54) SYSTEMS AND METHODS FOR CONTROLLING A VEHICLE OR DEVICE IN RESPONSE TO A MEASURED HUMAN RESPONSE TO A PROVOCATIVE ENVIRONMENT

(71) Applicant: Wesley W. O. Krueger, San Antonio, TX (US)

(72) Inventor: Wesley W. O. Krueger, San Antonio, TX (US)

(73) Assignee: IARMOURHOLDINGS, INC., San Antonio, CA (US)

( * ) Notice: Subject to any disclaimer, the term of this patent is extended or adjusted under 35 U.S.C. 154(b) by 118 days.

(21) Appl. No.: 15/048,824

(22) Filed: Feb. 19, 2016

(65) Prior Publication Data
US 2016/0167672 A1 Jun. 16, 2016

Related U.S. Application Data

(63) Continuation-in-part of application No. 14/172,734, filed on Feb. 4, 2014, now Pat. No. 9,298,985, which
(Continued)

(51) Int. Cl.
B60W 40/08 (2012.01)
G02B 27/01 (2006.01)
(Continued)

(52) U.S. Cl.
CPC .............. B60W 40/08 (2013.01); A61B 3/145 (2013.01); A61B 5/02055 (2013.01); A61B 5/0402 (2013.01); A61B 5/0476 (2013.01);
A61B 5/18 (2013.01); A61B 5/4023 (2013.01); A61B 5/4863 (2013.01); A61B 5/6803 (2013.01);
(Continued)

(58) Field of Classification Search
CPC ........ G02B 27/017; B60W 2040/0818; B60W 2040/0872
See application file for complete search history.

(56) References Cited

U.S. PATENT DOCUMENTS 3,157,852 A 11/1964 Hirsch
4,028,725 A 6/1977 Lewis
(Continued)

Primary Examiner — Thaddeus Cox
(74) Attorney, Agent, or Firm — Kilpatrick Townsend & Stockton LLP

(57) ABSTRACT

A sensor system and method for determining if an environment is provocative, measuring a human response to this environment, and controlling a vehicle or device is disclosed. The system and method comprise a human head-worn unit with an orientation sensing element, a head-attachable display comprising a first image not responsive to pitch and roll and a display element responsive to the orientation sensing element. The system and method also comprises at least one human response sensor such as a galvanic skin response sensor, a blood pressure sensor, or an electroencephalograph. The system and method further comprise an algorithm that computes a signal that is a measure of the condition of the human based on input from the orientation sensing element and the human response sensor or sensors. The system and method also comprise an electronic interface configured for transmitting the human physical condition signal.

17 Claims, 10 Drawing Sheets

Related U.S. Application Data is a continuation-in-part of application No. 13/108,683, filed on May 16, 2011, now Pat. No. 8,690,750.

(60) Provisional application No. 62/177,070, filed on Mar. 4, 2015, provisional application No. 61/345,040, filed on May 14, 2010.

(51) Int. Cl.

| | |
|---|---|
| *A61B 5/0205* | (2006.01) |
| *A61B 5/00* | (2006.01) |
| *A61B 5/0476* | (2006.01) |
| *A61B 3/14* | (2006.01) |
| *A61B 5/0402* | (2006.01) |
| *A61B 5/18* | (2006.01) |
| *H04N 13/04* | (2006.01) |
| *G06T 19/00* | (2011.01) |
| *A61M 21/00* | (2006.01) |
| *G01C 23/00* | (2006.01) |
| *G06K 9/00* | (2006.01) |

(52) U.S. Cl.
CPC .......... *A61B 5/7282* (2013.01); *A61B 5/7405* (2013.01); *A61B 5/746* (2013.01); *A61B 5/7425* (2013.01); *A61B 5/7445* (2013.01); *A61B 5/7455* (2013.01); *A61M 21/00* (2013.01); *G01C 23/00* (2013.01); *G02B 27/017* (2013.01); *G06K 9/00604* (2013.01); *G06T 19/006* (2013.01); *H04N 13/044* (2013.01); *H04N 13/0468* (2013.01); *A61M 2021/0022* (2013.01); *A61M 2021/0027* (2013.01); *A61M 2021/0044* (2013.01); *A61M 2021/0083* (2013.01); *A61M 2205/18* (2013.01); *A61M 2205/332* (2013.01); *A61M 2205/3306* (2013.01); *A61M 2205/3317* (2013.01); *A61M 2205/3569* (2013.01); *A61M 2205/3592* (2013.01); *A61M 2205/507* (2013.01); *A61M 2210/0612* (2013.01); *A61M 2230/04* (2013.01); *A61M 2230/10* (2013.01); *A61M 2230/20* (2013.01); *A61M 2230/201* (2013.01); *A61M 2230/205* (2013.01); *A61M 2230/207* (2013.01); *A61M 2230/208* (2013.01); *A61M 2230/30* (2013.01); *A61M 2230/40* (2013.01); *A61M 2230/432* (2013.01); *A61M 2230/435* (2013.01); *A61M 2230/50* (2013.01); *A61M 2230/60* (2013.01); *A61M 2230/62* (2013.01); *A61M 2230/63* (2013.01); *A61M 2230/65* (2013.01); *B60W 2040/0872* (2013.01); *G02B 2027/014* (2013.01); *G02B 2027/0138* (2013.01); *G02B 2027/0187* (2013.01); *G06K 9/00671* (2013.01)

(56) References Cited

U.S. PATENT DOCUMENTS

| | | | |
|---|---|---|---|
| 4,326,189 | A | 4/1982 | Crane |
| 5,051,735 | A | 9/1991 | Furukawa |
| 5,067,941 | A | 11/1991 | Hendricks |
| 5,486,821 | A | 1/1996 | Stevens et al. |
| 5,583,795 | A | 12/1996 | Smyth |
| 5,599,274 | A | 2/1997 | Widjaja et al. |
| 5,629,848 | A | 5/1997 | Repperger et al. |
| 5,635,947 | A | 6/1997 | Iwamoto |
| 5,790,085 | A | 8/1998 | Hergesheimer |
| 5,966,680 | A | 10/1999 | Butnaru |
| 6,228,021 | B1 | 5/2001 | Kania |
| 6,361,508 | B1 | 3/2002 | Johnson et al. |
| 6,364,845 | B1 | 4/2002 | Duffy et al. |
| 6,443,913 | B1 | 9/2002 | Kania |
| 6,497,649 | B2 | 12/2002 | Parker et al. |
| 6,568,396 | B1 | 5/2003 | Anthony |
| 6,896,655 | B2 | 5/2005 | Patton et al. |
| 6,924,428 | B1 | 8/2005 | Kania |
| 6,932,090 | B1 | 8/2005 | Reschke et al. |
| 7,128,705 | B2 | 10/2006 | Brendley et al. |
| 7,183,946 | B2 | 2/2007 | Boudrieau |
| 7,266,446 | B1 | 9/2007 | Pelosi |
| 7,331,671 | B2 | 2/2008 | Hammoud |
| 7,474,335 | B2 | 1/2009 | Basson et al. |
| 7,490,611 | B2 | 2/2009 | Bromwich |
| 7,643,394 | B2 | 1/2010 | Neely et al. |
| 7,667,700 | B1 | 2/2010 | Neely et al. |
| 7,717,841 | B2 | 5/2010 | Brendley et al. |
| 7,722,526 | B2 | 5/2010 | Kim |
| 7,893,935 | B1 | 2/2011 | Neely et al. |
| 7,925,391 | B2 | 4/2011 | Sanders-Reed |
| 8,063,798 | B2 | 11/2011 | Cernasov et al. |
| 8,218,006 | B2 | 7/2012 | De Mers et al. |
| 2001/0028309 | A1 | 10/2001 | Torch |
| 2006/0253001 | A1 | 11/2006 | Small et al. |
| 2009/0312817 | A1 | 12/2009 | Hogle et al. |
| 2009/0326604 | A1 | 12/2009 | Tyler et al. |
| 2011/0028872 | A1 | 2/2011 | Kevin |
| 2011/0029045 | A1 | 2/2011 | Cevette et al. |
| 2011/0045446 | A1 | 2/2011 | Glaser et al. |
| 2014/0176296 | A1* | 6/2014 | Morgan ............... G06F 3/011 340/4.13 |
| 2014/0268356 | A1* | 9/2014 | Bolas ............... G02B 27/0093 359/630 |
| 2016/0178904 | A1* | 6/2016 | Deleeuw ............... H04N 13/044 345/8 |
| 2017/0146797 | A1* | 5/2017 | Samuthirapandian ............ G02B 27/0101 |
| 2017/0192235 | A1* | 7/2017 | Petrov ............... G02B 27/0172 |

* cited by examiner

Centered    Pitch down    Roll left    Yaw left

| Centered | Pitch down | Roll left | Yaw left |
|---|---|---|---|
| 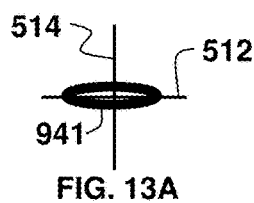 | 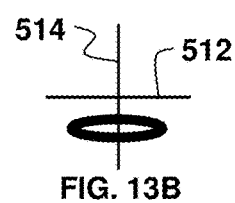 | 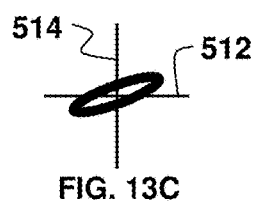 | 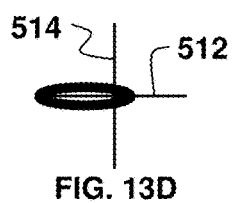 |
| FIG. 13A | FIG. 13B | FIG. 13C | FIG. 13D |
| 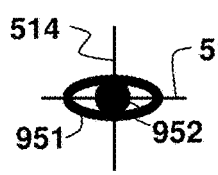 | 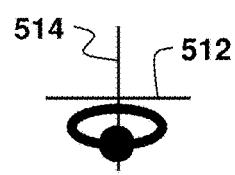 | 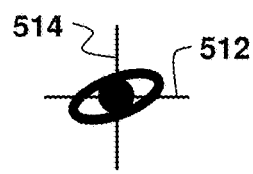 | 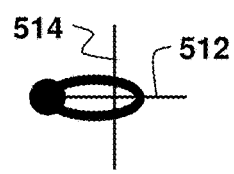 |
| FIG. 14A | FIG. 14B | FIG. 14C | FIG. 14D |
| 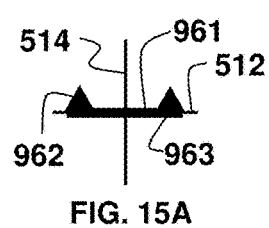 | 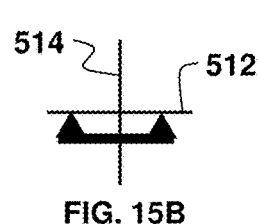 | 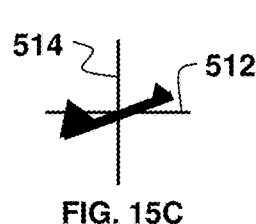 | 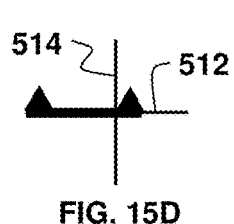 |
| FIG. 15A | FIG. 15B | FIG. 15C | FIG. 15D |
| 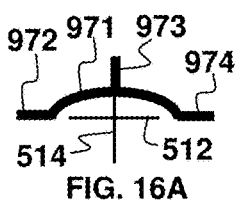 | 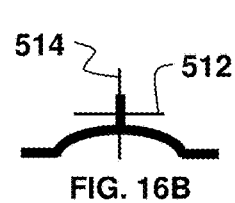 | 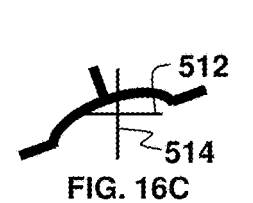 | 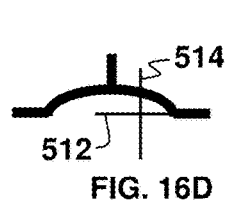 |
| FIG. 16A | FIG. 16B | FIG. 16C | FIG. 16D |

SYSTEMS AND METHODS FOR CONTROLLING A VEHICLE OR DEVICE IN RESPONSE TO A MEASURED HUMAN RESPONSE TO A PROVOCATIVE ENVIRONMENT

CROSS-REFERENCE TO RELATED APPLICATIONS

This application claims the benefit of U.S. Provisional Patent Application Ser. No. 62/177,070 filed 4 Mar. 2015, and is a continuation-in-part of U.S. patent application Ser. No. 14/172,734, filed Feb. 4, 2014, now U.S. Pat. No. 9,298,985, issued Mar. 29, 2016, which is a continuation-in-part of U.S. patent application Ser. No. 13/108,683 filed May 16, 2011, now U.S. Pat. No. 8,690,750, which claims the benefit of U.S. Provisional Patent Application Ser. No. 61/345,040 filed May 14, 2010, the entire disclosures of which are incorporated by reference herein.

BACKGROUND

This disclosure relates to electronic systems and methods to measure, mitigate, and respond to human indicators of unhealthiness in provocative environments. Provocative environments can result from vehicle motion, other stimuli in a person's environment, and/or viewing computer-generated images. The images could be in a virtual reality (VR), an augmented reality (AR), a multi-dimensional (MD), or a synthetic environment.

Motion sickness, spatial disorientation (SD), vertigo, and other motion-induced conditions are a widespread problem. Up to 60% of people have some motion intolerance. Motion sickness affects nearly one third of people who travel by land, sea, or air. Individuals get motion sick and spatially disoriented while riding or driving/piloting cars, trains, buses, planes, boats, or other vehicles. 10 million US patients receive balance (vertigo) therapy costing $1 billion annually. Reasons for treatment are due to disease affecting the vestibular organs, rehabilitation from surgery on the balance organs, recovery from trauma to the head and rehabilitation in patients learning to use prosthetics in the lower extremities.

SD and motion sickness are significant problems in aviation, affecting human performance (cognitive and motor skills) and resulting in the loss of expensive aircraft and human life. Thousands of deaths have been attributed to accidents caused by SD. A recent study showed that 90%-100% of aircrews reported at least one incidence of SD during their flying careers. SD accounted for 11%-14% of USAF mishaps and a mishap fatality rate of 69%, with risk of SD significantly increased in helicopters and fighter/attack aircraft and at night. The most frequent experienced SD episodes are "leans" (92%), loss of horizon due to atmospheric conditions (82%), misleading altitude cues (79%), sloping horizon (75%), and SD arising from distraction (66%). Airsickness has also been identified as a flight training issue. A motion sickness history questionnaire obtained from student pilots in the Air Force revealed an incidence of airsickness of 50%. In a questionnaire to B-1 and B-52 bomber crewmembers, it was reported to be a frequent occurrence among non-pilots in both aircraft, and experienced crewmembers were more likely to report an impact on their duties.

Space motion sickness is experienced by 60%-80% of astronauts during the first two to three days in micro gravity and by a similar proportion during their first few days after return to Earth. Up to 90% of astronauts experienced spatial disorientation during reentry and landing of the shuttle, with prevalence proportional to the length of the mission. Exposure to micro gravity rearranges the relationships among signals from visual, skin, joint, muscle, and vestibular receptors. Congruence between vestibular signals and those from other receptors, as well as between the vestibular otolith and semicircular canal receptors, is disrupted by the absence of gravity. This lack of congruence between sensory exposure to provocative real or apparent motion leads to the progressive cardinal symptoms of terrestrial motion sickness. Space motion sickness may vary slightly with flushing more common than pallor, stomach awareness, malaise, loss of appetite, and sudden vomiting, often without prodromal nausea.

Simulator sickness can be another example of motion sickness. Many military pilots have reported at least one symptom following simulator exposure. In a study of Coast Guard aviators undergoing flight simulator testing, 64% reported adverse symptoms during the first simulator flight and 39% did so during the last flight. 36% of pilots reported motion sickness when training on a Blackhawk flight simulator. More recently, simulator sickness in virtual environments (VE) has become an important issue. VR is already a popular technology for entertainment purposes, and both the U.S. Army and Navy are interested in the training applications of VEs. However, some users of VE experience discomfort during, and/or after, a session in a simulated environment, in equivalent fashion to simulator sickness already noted for flight and driving simulators.

VR sickness (also known as cyber sickness) occurs when exposure to a virtual environment causes symptoms similar to motion sickness symptoms. VR sickness may have undesirable consequences beyond the sickness itself. For example, flight simulator sickness can discourage pilots from using flight simulators, reduce the efficacy of training through distraction, encourage adaptive behaviors unfavorable for performance, and compromise ground safety or flight safety when sick and disoriented pilots leave the simulator. Similar consequences could be expected for VR systems. VR sickness can be a major barrier to using VR, indicating that VR sickness may be a barrier to the effective use of training tools and rehabilitation tools in VR. There are various technical aspects of VR, AR, MD and synthetic environments that can induce visually induced motion sickness (VIMS), such as mismatched motion, field of view, motion parallax, and viewing angle. The amount of time spent in VR, AR, MD and synthetic environments can increase the presence of symptoms. Possible adverse motion-related health effects from VR, AR, MD or synthetic environments can include photosensitive seizures, VIMS, and eyestrain.

Vection has been found to be correlated with levels of VIMS and postural status. The correlation between vection and VIMS has led to the term vection induced motion sickness. Visually induced vection can be quite compelling, and the illusion has been investigated extensively for over a century. Although false perceptions of self-motion are common in a VR, AR, MD or synthetic environment, visual characteristics linked to this type of illusion are not fully understood. Vection can be strongly influenced by various physical aspects. Rotating auditory cues can also induce vection but auditory vection can be much weaker and far less compelling than visual vection, which can be indistinguishable from real motion.

BRIEF DESCRIPTION OF THE DRAWINGS

The present invention can be better understood by reading the detailed description of non-limiting embodiments, and on examining the accompanying drawings, in which:

FIG. 8A illustrates an embodiment of a Head Attitude Scale (HAS);

FIG. 8B illustrates an embodiment of a Pitch/Roll Indicator (PRI) with a vertical fin;

FIG. 8C illustrates an alternative embodiment of a Pitch/Roll Indicator (PRI) with a vertical fin;

FIG. 8D illustrates an embodiment of a Pitch/Roll Indicator (PRI) in conjunction with a HAS;

FIG. 8E illustrates an alternate embodiment of a Pitch/Roll Indicator (PRI) in conjunction with a HAS;

FIG. 8F illustrates an embodiment of a Head-Rotation/Yaw Indicator in conjunction with a Pitch Roll Indicator;

FIG. 8G illustrates an embodiment of a Head-Rotation/Yaw Indicator in conjunction with a Pitch Roll Indicator and a HAS;

FIG. 8H illustrates the embodiment of the symbology of FIG. 8G reflecting different positional circumstances; and FIG. 8I illustrates another embodiment of a Pitch/Roll Indicator (PRI) in conjunction with a HAS;

FIG. 9A through FIG. 16D illustrate additional embodiments of display symbologies, in which, more specifically:

FIG. 9A, FIG. 9B, FIG. 9C, and FIG. 9D show a display symbology in which the Pitch Roll Indicator can be three circles in a line in a centered, pitch down, roll left, and yaw left view, respectively;

FIG. 13A, FIG. 13B, FIG. 13C, and FIG. 13D show a display symbology in which the Pitch Roll Indicator can be an ellipse in a centered, pitch down, roll left, and yaw left view, respectively;

FIG. 14A, FIG. 14B, FIG. 14C, and FIG. 14D show a display symbology in which the Pitch Roll Indicator can be a horizontal ellipse and a solid circle in a centered, pitch down, roll left, and yaw left view, respectively;

FIG. 15A, FIG. 15B, FIG. 15C, and FIG. 15D show a display symbology in which the Pitch Roll Indicator can be a horizontal line with two triangles in a centered, pitch down, roll left, and yaw left view, respectively;

FIG. 16A, FIG. 16B, FIG. 16C, and FIG. 16D show a display symbology in which the Pitch Roll Indicator can be a half ellipse and three line segments in a centered, pitch down, roll left, and yaw left view, respectively; In FIG. 17A, there is no pitch, roll or yaw. In FIG. 17B, there is pitch downward and yaw to the left.

Figure 1:
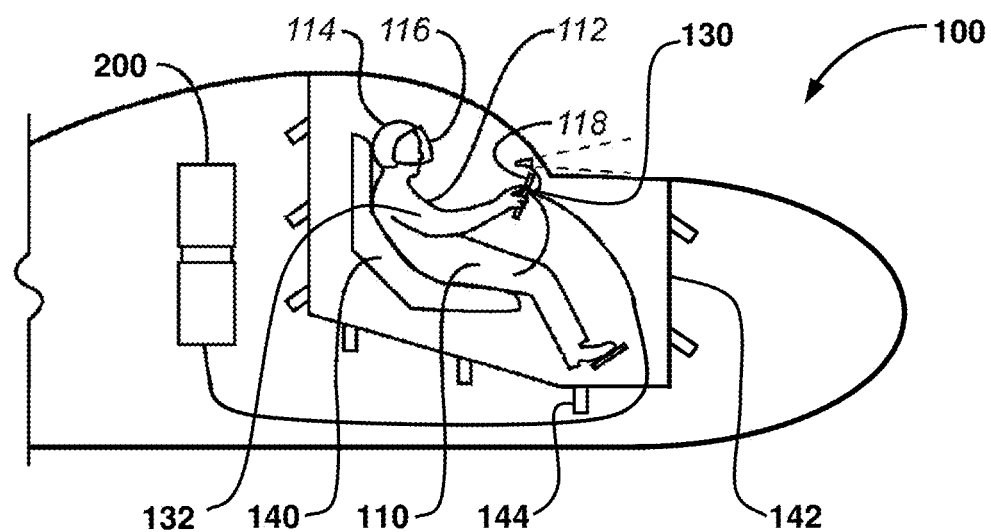
FIG. 1 illustrates an exemplar environment that can be provocative, causing an unhealthy human response.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

1. OVERVIEW

The present invention generally relates to systems and methods for measuring, mitigating, and responding to human indicators of unhealthiness in provocative environments. The provocative environment can be created through vehicle motion, other stimuli in a person's environment, and/or when someone views computer-generated images. The computer-generated images could be in a virtual reality (VR), an augmented reality (AR), a multi-dimensional (MD), or a synthetic environment. The systems and methods could measure head pitch and roll, and they could include additional measures of position and/or orientation. The systems and methods could comprise a display. The display could comprise a first image that is not responsive to measures of position and/or orientation of the person's head. The display could comprise a second image that is responsive to position and/or orientation of the person's head. The system or method could measure environmental inputs other than head position and/or orientation, to determine if the environment is provocative. The systems or methods could measure physiologic factors to determine if a person is experiencing an unhealthy physical response due to motion-related sensory mismatch. Indicators of unhealthy physical responses can include blood chemistry, blood pressure, body temperature, brain electrical activity, eye and/or eyelid movement, heart rate and other measures of heart function, hydration, respiratory activity, respiratory chemistry, changes in level of orientation, changes in consciousness, changes in the attention state, disorientation, dizziness, drowsiness, difficulty with focusing, fuzziness, inattentiveness, loss of situation awareness, motion intolerance, motion sickness, nausea, sensory conflict or sensory mismatch disorder, spatial disorientation (SD), user disabilities, vertigo, visually-induced motion sickness, or other complaints such as not being clear headed. The systems or methods could provide feedback on a display. The determination of the person's health condition could control a vehicle or device.

Examples of the environmental factors that could be measured by the system and method, to determine if the environment is provocative, can include, but are not limited to, factors and sensors in the list below.

a. Head orientation (pitch, roll and yaw) and other measurements of position and orientation can be measured with a head tracker or trackers. Such head tracker or trackers could measure position, orientation, velocity, rotational velocity, linear acceleration, angular acceleration, vibration, and other parameters related to the head of the subject resulting from movement of the person's environment. The head tracker can use one or more accelerometers and these could be MEMS (micro electro mechanical systems) accelerometers such as the Analog Devices ADXL202E, which can measure both dynamic acceleration (e.g., vibration) and static acceleration (e.g., gravity). The outputs are analog voltage or digital signals whose duty cycles (ratio of pulse width to period) are proportional to acceleration. A microprocessor counter, without an A/D (analog to digital) converter or glue logic, can directly measure the duty cycle outputs. The duty cycle period can be adjustable from 0.5 ms to 10 ms via external timing resistor. The ADXL202E can be a complete, dual-axis acceleration measurement system. For each axis, an output circuit converts the analog signal to a duty cycle modulated (DCM) digital signal that can be decoded with the timer port of the microprocessor used. The ADXL202E can be capable of measuring both positive and negative accelerations to at least ±2 g. The accelerometer can measure static acceleration forces such as gravity, allowing it to be used as a tilt sensor as used in our application. Acceleration will result in an output square wave whose amplitude can be proportional to acceleration. The duty cycle period can be adjustable from 0.5 ms to 10 ms via external timing resistor. The ADXL202E can be a complete, dual-axis acceleration measurement system. For each axis, an output circuit converts the analog signal to a duty cycle modulated (DCM) digital signal that can be decoded with the timer port of the microprocessor used. The ADXL202E can be capable of measuring both positive and negative accelerations to at least ±2 g. The accelerometer can measure static acceleration forces such as gravity, allowing it to be used as a tilt sensor as used in our application. Acceleration will result in an output square wave whose amplitude can be proportional to acceleration. Phase sensitive demodulation techniques are then used to rectify the signal and determine the direction of the acceleration. In addition to accelerometers, head trackers can include magnetometers, gyroscopes, optical sensors, and devices that use the global positioning system (GPS). The gyroscope may include a micro-electromechanical system (MEMS) gyroscope or a fiber optic gyroscope. The GPS unit may include a receiver that obtains clock and other signals from GPS satellites.

b. Air pressure (for example cabin pressure in an aircraft or spacecraft, or altitude) can be measured using an air pressure sensor which can incorporate: a piezoresistive strain gage; a capacitive diaphragm; an electromagnetic diaphragm using inductance, a linear variable differential transformer (LVDT), a hall effect sensor, an eddy current sensor; a piezoelectric strain measurement device; a optical technique; a potentiometric wiper; a resonance; thermal conductivity measurement; an ionization measurement; a manometer, or any other measurement technology capable of being understood by anyone skilled in the art.

c. Air chemistry could be measured using any sensor capable of being understood by anyone skilled in the art. For examples:
  carbon dioxide can be measured using a MEMS (micro electro mechanical system) sensor or an infrared sensor;
  carbon monoxide can be measured opto-chemically, biomimetically, electrochemically, or using semiconducting tin-oxide on an insulating ceramic base;
  nitrogen (and other gases) can be measured using gas chromatography, thermal conductivity, or an optical sensor;
  organophosphate levels (and other chemicals) can be measured using ion mobility spectroscopy (IMS) and differential ion mobility spectroscopy (DMS); and
  oxygen can be measured using an electro-galvanic fuel cells;

d. Electromagnetic radiation sensors could measure visible or ultraviolet light frequency and/or intensity. These sensors can be placed on the skin, on any human worn item, in the vehicle, or in some other part of the local environment such as inside or outside of a vehicle. Examples of skin-worn sensors include the Microsoft Band and the Laroche-Posay UV Patch. Electromagnetic radiation can be measured using sensors that measure intensity at a specific frequency or sensors that measure overall light level, such as photoreceptors and laser sensors.

e. Laser light could be detected by sensors located on the eyewear, on a head worn device, or within the lenses covering the eyes. Visible light (380 to 750 nanometers) from lasers can enter the optical system and can be magnified and focused on the back of the eye (retina), making the retina the target of the laser energy. Non-visible light can be in the wavelength range of ultraviolet (200 to 380 nanometers), near infrared (750 to 1,400 nanometers), or mid to far infrared (1,400 nanometers to 1 millimeter). The eye's natural defense for bright visible light is to blink, which can take effect within a quarter of a second. Non-visible laser light can enter the optical system and affect the eye, but it isn't visible and therefore presents a different challenge because the blink response only works with visible light. Near infrared light has the same effect on the retina as visible light, but cannot be seen. Ultraviolet and mid- to far-infrared wavelengths affect the cornea and lens and can cause corneal clouding or cataracts. At low intensities, visible light from lasers can cause glare, an interference that inhibits the viewer from seeing details in the visual scene due to excess brightness. At high brightness, visible light from lasers preclude a viewer from seeing outside landmarks and references, such as with pilots, and can affect their ability to clearly see an instrument panel directly in front of them. Green light at 555 nanometers is the most visible (100%). Most green consumer laser pointers emit 532 nm light. Eyewear absorbing 532 nm typically has an orange appearance, transmitting wavelengths larger than 550 nm. Such eyewear would be useless as protection against a laser emitting at 800 nm. Some lasers emit more than one wavelength of light. Smart photoreceptors, photoelectric devices, and laser sensors could detect the wavelength of the emitted light and transmit this information to receptors on the lens or framework around the lenses, which change the lens to alter the wavelength of the emitted light, protecting the person's eyes. The smart sensors could detect single wavelength or multiple wavelengths to ultimately activate a blocking process based on the incoming wavelength(s) of light. For example, theses smart lenses, responsive to the transmitted wavelength information from the sensor, can prevent the laser light from reaching the eye by various photochromic or electrochemical methods.

f. Orientation, position, orientation change rate, and position change rate sensors in addition to those already mentioned for head orientation can include global positioning system (GPS) devices, magnetometers, optical devices, accelerometers, and gyroscopes. Changes in position and orientation between one part of the environment and another (such as between a steering device and the rudder of a plane) can also be measured using mechanical transducers that measure things such as strain, hydraulic oil pressure, shaft rotation, and other mechanical movement capable of being understood by anyone skilled in the art.

g. Temperature in the environment can be measured by any of a variety of instruments and/or sensors including thermocouples, thermistors, resistance temperature detectors, pyrometers, infrared sensors, thermometric materials, silicon band gap sensors, liquid thermometers, and gas thermometers.

Human response (or outputs) to a potentially provocative environment can be measured by looking at a variety of physical or physiologic factors. Chemical indicators in the blood are one example of these physical or physiologic factors. Among the chemical indicators are ones that measure the blood chemistries in the list below.

Blood alcohol can be measured from a person's breath or on the skin surface using a sensor such as the electrochemical sensor made by Giner technologies. The skin sensors could be part of a head-worn unit or placed anywhere on a person's skin. Blood Alcohol Level (BAL) can be recorded in milligrams of alcohol per 100 milliliters of blood, or milligrams percent. The BAL of 0.10 means that 1/10 of 1 percent of the total blood content is alcohol. Blood alcohol can be measured optically using near-infrared (NIR) absorption spectroscopy. Optical measurement begins when the sensor touches the operator, which illuminates the operator's skin with NIR light, which propagates into the tissue. The beam of light can penetrate tissue at depths of up to 5 mm to reach the dermal layer where alcohol that is dissolved in water resides. A portion of the light is diffusely reflected back to the skin's surface and collected by an optical touch pad. The light contains information on the unique chemical information and tissue structure of the user. This light is analyzed to determine the alcohol concentration. It can also be used to verify the identity of a person.

Blood amino acids can be measured from saliva or from the blood using a chromatograph or a molecular imprinted polymer. Among the amino acids, which could be measured, are alanine, alpha-aminoadiphic acid, alpha-amino-N-butyric acid, arginine, asparagine, aspartic acid, beta alanine, beta-amino-isobutyric acid, carnosine, citrulline, cystine, glutamic acid, glutamine, glycine, histidine, hydroxyproline, isoleucine, leucine, lysine, methionine, 1-methylhistidine, 3-methylhistidine, ornithine, phenylalanine, phosphoserine, phosphoethanolamine, proline, serine, taurine, threonine, tyrosine, and valine.

Blood calcium can be measured on the skin surface using skin sensors, such as those made by Eccrine Systems.

Blood carbon dioxide can be measured using a skin sensor such as those made by Giner technologies.

Blood catecholamines, such as dopamine, can be measured on the skin surface with an electrochemical sensor using molecular imprinted polymers (MIPs).

Blood chloride, which can measure hydration and detect electrolyte abnormalities, can be measured using a skin sensor such as those made by Eccrine Systems.

Blood cortisol, which is a steroid in the brain related to stress, can be measured on the skin surface using a skin sensor that measures cortisol in one's sweat, such as the sensors made be Eccrine Systems.

Blood creatinine, which can be used to determine kidney function, can be measured using a skin sensor such as those made by Eccrine Systems.

Blood dehydroepiandrosterone (DHEA), which can help regulate hormone function, can be measured from a person's saliva or on their skin, or their finger or toenails.

Blood electrolyte levels can be determined by measuring blood chloride, blood potassium, or blood sodium as described in other parts of this disclosure.

Blood glucose can be measured using a skin sensor such as the ones made by Echo Therapeutics.

Blood hematocrit can be measured using an optical sensor.

Blood hemoglobin can be measured on the skin using a pulse oximetry device, or using any technology capable of being understood by anyone skilled in the art, including the signal extraction technology developed by Masimo. Another non-invasive instrument can be the POC portable hemoglobin analyzer from MBR Optical Systems.

Blood lactate concentration can be measured using a sensor such as those developed by Eccrine Systems.

Blood oxygen saturation is a term referring to the fraction of oxygen-saturated hemoglobin relative to total hemoglobin (unsaturated+saturated) in the blood. More simply blood oxygen saturation level refers to the percentage of a person's red blood cells that are loaded or filled with oxygen. Oxygen is carried by the red blood cells to organs, such as the brain and the heart. If the blood oxygen level is too low, not enough oxygen is carried to the organs. Without an adequate blood oxygen level, the body cannot function normally. The human body requires and regulates a very precise and specific balance of oxygen in the blood. Normal blood oxygen levels in humans are considered 95-100 percent. If the level is below 90 percent, it is considered low resulting in hypoxemia. Blood oxygen levels below 80 percent may compromise organ function, such as the brain and heart, and should be promptly addressed. Continued low oxygen levels may lead to respiratory or cardiac arrest. Oxygen therapy may be used to assist in raising blood oxygen levels. Oxygenation occurs when oxygen molecules enter the tissues of the body. For example, blood is oxygenated in the lungs, where oxygen molecules travel from the air and into the blood. Oxygen saturation, commonly referred to as "sats," measures the percentage of hemoglobin binding sites in the bloodstream occupied by oxygen. At low partial pressures of oxygen, most hemoglobin is deoxygenated. A pulse oximeter relies on the light absorption characteristics of saturated hemoglobin to give an indication of oxygen saturation. Hypoxemia is a below-normal level of oxygen in your blood, specifically in the arteries. Hypoxemia is a sign of a problem related to breathing or circulation, and may result in various symptoms, such as shortness of breath. Hypoxemia is determined by measuring the oxygen level in a blood sample taken from an artery (arterial blood gas). It could also be estimated by measuring the oxygen saturation of your blood using a pulse oximeter device including the signal extraction technology developed by Masimo and that developed by Kestrel Labs or with a device using photoplehtysmography (PPG), using such devices which clips to your finger or can be placed on your ear lobe or in the ear canal or can use any other technology capable of being understood by anyone skilled in the art.

Blood PH can be measured on the skin surface using skin sensors such as the Sweatronics Platform manufactured by Eccrine Systems.

Blood potassium, which can be indicative of electrolyte abnormalities, can be measured using a skin sensor such as those made by Eccrine Systems.

Blood sodium concentration, which can be also indicative of electrolyte abnormalities, can be measured using a skin sensor such as those made by Eccrine Systems.

Blood uric acid, which can be indicative of gout, hyperuricemia, and Lesch-Nyhan syndrome, can be measured on the skin surface with an electrochemical sensor using molecular imprinted polymers (MIPs).

Each element of blood chemistry could be measured individually or multiple elements of blood chemistry could be combined. For example, embodiments of the present invention could be used to detect respiratory acidosis, a condition in which a build-up of carbon dioxide in the blood produces a shift in the body's pH balance and causes the body's system to become more acidic. This condition can be brought about by a problem either involving the lungs and respiratory system or signals from the brain that control breathing. In this type of acidosis, the pH will be below 7.35. The pressure of carbon dioxide in the blood will be high, usually over 45 mmHg. Sensors on the skin could detect the pH, oxygen saturation or percent (%) of oxygenation in the body.

Human response (or outputs) to a potentially provocative environment can be also determined by measuring other physical/physiologic factors, such as the ones listed below.

a. Blood pressure is the measure of the force of blood pushing against blood vessel walls. Blood pressure is usually expressed in terms of the systolic (maximum) pressure over diastolic (minimum) pressure and is measured in millimeters of mercury (mm Hg). Normal resting blood pressure in an adult is approximately 120/80 mm Hg. Blood pressure varies depending on situation, activity, and disease states. It is regulated by the nervous and endocrine systems. Blood pressure that is low due to a unhealthy state is called hypotension, and pressure that is higher than normal is called hypertension. Both have many causes which can range from mild to severe. The systolic pressure measures the pressure in the arteries when the heart beats (when the heart muscle contracts). The diastolic pressure measures the pressure in the arteries between heartbeats (when the heart muscle is resting between beats and refilling with blood). Hypertension is dangerous because it makes the heart work harder to pump blood out to the body and contributes to hardening of the arteries, or atherosclerosis, to stroke, kidney disease, and to the development of heart failure. Hypertension can be defined as a diastolic blood pressure greater than or equal to 120 mmHg (millimeters of mercury) and/or systolic blood pressure greater than or equal to 180 mmHg. Hypotension can be generally considered systolic blood pressure less than 90 mmHg and/or diastolic less than 60 mmHg. Blood pressure can be measured by a barosensor place on the skin over an artery. The barosensor could be could be implemented as a MEMS (micro electro mechanical sensor) device or an optical sensor and can measure pressure in the blood vessels. The measurement does not require using a blood pressure cuff but could use a MEMs barosensor placed over the superficial temporal artery, located above the ear canal and tragus near the attachment of the pinna. Any headworn or eye worn device placing some pressure against the barosensor could elicit a blood pressure measurement. An example of of such sensor could be the sapphire optoelectronic blood pressure sensor made by Tarilian Laser Technologies.

b. Body position and orientation can be measured using mechanoreceptors, which could measure mechanical changes in the body using a MEMS sensor such as that used in the HITS (head impact telemetry system) developed at Virginia Tech and Dartmouth College in 2002. Body position can also be measured using a GPS position measurement of a body part, or optical, magnetic, gyroscopic, or acceleration-based sensors. These sensors could be on any body part and could measure relative motion of various body parts to each other.

c. Brain activity can be measured using an electroencephalograph (EEG), which could record the electrical potential along the scalp produced by the neurons within the brain. EEG measurement can be done using any EEG technology capable of being understood by anyone skilled in the art. Some waveforms in the EEG signal are highly correlated with the individual's sleepiness level. Electrical activity emanating from the brain can be displayed in the form of brainwaves. There are four categories of these brainwaves, ranging from the most activity to the least activity: beta; alpha, theta and delta. When the brain is aroused and actively engaged in mental activities, it generates beta waves. These beta waves are of relatively low amplitude, and are the fastest of the four different brainwaves. Research has shown that although one brainwave state may predominate at any given time, depending on the activity level of the individual, the remaining three brain states are present in the mix of brainwaves at all times. In other words, while somebody can be in an aroused state and exhibiting a beta brainwave pattern, there also exists in that person's brain a component of alpha, theta and delta, even though these may be present only at the trace level.

d. Eye position and movement can be measured using a video camera that records images of the user's eyes as they move during use of the system. More detail of eye tracking embodiments and fields of use will be provided later in this disclosure.

e. Eyelid position and movement can also be measured using a video camera that records images of the user's eyelids as they move during use of the system. More eyelid position and movement embodiments will be provided later in this disclosure.

f. Other eye parameters can also be measured. One example can be retinal scanners, such as those made by Optos, which scan features of the back of the retina.

g. Heart function, which can include both heart rate and an electrocardiogram (ECG). The pulse can also be referred to as the heart rate, which is the number of times the heart beats each minute (bpm). But the rhythm and strength of the heartbeat can also be noted, as well as whether the blood vessel feels hard or soft. Changes in the heart rate or rhythm, a weak pulse, or a hard blood vessel may be caused by heart disease or another problem. Heart rate is therefore the speed of the heartbeat measured by the number of contractions of the heart per unit of time. The heart rate can vary according to the body's physical needs, including the need to absorb oxygen and excrete carbon dioxide. It is usually equal or close to the pulse measured at any peripheral point away from the heart. Factors that can provoke changes in heart rate, or pulse rate, can include physical exercise, sleep, anxiety, stress, illness, heart disease, physical trauma, blood loss, oxygen levels in the blood as well as other human chemical or physical changes and drugs. The normal resting adult human heart rate ranges from 60-100 bpm. Tachycardia is a fast heart rate, defined as above 100 bpm at rest. Bradycardia is a slow heart rate, defined as below 60 bpm at rest. During sleep a slow heartbeat with rates around 45-50 BPM is common and may be considered normal. Bradycardia can be seldom symptomatic until the rate drops below 45 BPM. Bradycardia can result in fatigue, weakness, dizziness, and at very low rates fainting. When the heart beats excessively or rapidly, the heart pumps less efficiently and provides less blood flow to the rest of the body, including the heart itself. The increased heart rate also leads to increased work and oxygen demand by the heart, which can lead to rate related ischemia. When the heart is not beating in a regular pattern, this is referred to as an arrhythmia. These abnormalities of heart rate often indicate disease or an abnormal condition or parameter. During an arrhythmia, the heart can beat too fast, too slow, or with an irregular rhythm. Some cause few or minimal symptoms. Others produce more serious symptoms of light-headedness, dizziness and fainting. The heart's electrical system controls the rate and rhythm of the heartbeat. Heart rate gives a simple measure of heart function that can be measured using a simple electrically conductive sensor that measures electrical signals in the skin or changes in blood pressure to get a pulse. One example of such a sensor can be the Polar Electro hear rate monitor. An electrocardiogram, also called an EKG or ECG, is a simple, painless test that records the heart's electrical activity. With each heartbeat, an electrical signal spreads from the top of the heart to the bottom. As it travels, the signal causes the heart to contract and pump blood. The process repeats with each new heartbeat. This test checks for problems with the electrical activity of the heart. An EKG shows the heart's electrical activity as line tracings on paper and the spikes and dips in the tracings are called waves, which represent various areas of the heart's electrical activity. The right and left atria or upper chambers make the first wave called a "P wave", following a flat line when the electrical impulse goes to the bottom chambers. The right and left bottom chambers or ventricles make the next wave called a "QRS complex." The final wave or "T wave" represents electrical recovery or return to a resting state for the ventricles. An ECG gives two major kinds of information. First, by measuring time intervals on the ECG, it can be determined how long the electrical wave takes to pass through the heart. Finding out how long a wave takes to travel from one part of the heart to the next shows if the electrical activity is normal or slow, fast or irregular. Second, by measuring the amount of electrical activity passing through the heart muscle it can be possible to be able to find out if parts of the heart are too large or are overworked. An ECG, which could be implemented using any ECG technology capable of being understood by anyone skilled in the art, gives a more detailed view of the propagation of electrical waves in the heart, but requires that the electrodes are placed on the chest, proximate to the heart.

h. Respiratory chemistry, such as expired carbon dioxide and expired oxygen, can be measured on the face mask or on the helmet using sensors made by companies such as Philips Respironics or Analox Sensor Technology.

i. Respiratory rate can be measured on the skin surface, or it could be measured on the mask of a helmet. It can also be measured using piezo respiratory sensors or chest and abdominal movement sensing belts, such as those made by Gereonics.

j. Skin parameters, such as touch, vibration, position, and/or sense can be measured with proprioceptive sensors placed on a skin surface, an example of which might be the iSkin sensors developed by Saarland University and Carnegie Mellon University;

k. Galvanic skin response sensors (GSR) can measure characteristics such as stress, anxiety, hydration, and electrodermal activity. The GSR sensor is based on the principle of the Wheatstone bridge, a type of ohm meter for measuring changes in electrical resistance. The nervous system uses electrical impulses which are affected by the person's thoughts, emotions and physical condition. The GSR meter passes a tiny electrical carrier wave (approx. 0.5-3.0 volts) through the body, which picks up the fluctuations in resistance caused by the person's overall general mood and emotional reactions to specific stimuli. These changes in resistance are known as the galvanic skin response. Different emotional situations, such as stress or anxiety can lead the person suffering them to dangerous situations. This may be detected by an increase in the measured electrical resistance. For example, stress increases the risk of cardiac problems. Monitoring GSR response activity could enable the user to alter their activity or emotion by having such a measured response. Galvanic Skin Response (GSR) sensors could be referred to as stress sensors but also could measure, how much you sweat, which can be correlated with hydration or dehydration states and with calculation of exertion levels of a human to provide information of an unhealthy status. These sensors could be placed on the skin of the head or scalp and could be similar to the Microsoft Band or like that of Jawbone. Measurement could provide information such as wave detection of level of onset, onset latency for each wave, amplitude of each wave, peak latency of each wave. Predictably 5K ohms can indicate a high level of brain arousal (associated with a tense level) and values higher than 25K ohms can indicate low arousal and withdrawal from the mind (calm level).

l. Skin temperature can be measured by skin sensors such as those made by Maastricht Instruments. The skin temperature sensor could incorporate a thermistor.

The measurement of environmental input and human response parameters can be performed using sensors in contact with the user or remote sensors such as cameras. The sensors could be on the head-worn unit, part of some other wearable device on the user, or remote from the user. Cameras can include still image cameras, moving image cameras (such as video cameras), cameras that record information electronically, and cameras that record information chemically. Electronic can include digital electronics and analog electronics. Embodiments of the present invention can have the ability to control powered systems, such as vehicles or tools, or devices operated by the user. The user could be in a non-computer generated visual environment or while wearing, using, experiencing, or engaging in any visual platform or environment that comprises computer-generated images.

Embodiments of the present invention can use nanoscale sensors. Hybridization of nanoscale metals and carbon nanotubes into composite nanomaterials has produced some of the best-performing biosensors to date. A scalable nanostructured biosensor based on multilayered graphene petal nanosheets (MGPNs), Pt nanoparticles, and a biorecognition element (glucose oxidase) could be used in embodiments of the invention disclosed herein. The combination of zero-dimensional nanoparticles on a two-dimensional support that can be arrayed in the third dimension creates a biosensor platform with exceptional characteristics.

2. DEFINITIONS

Augmented reality (AR) is the superimposition of a computer-generated image on a user's view of the real world to provide a composite view. Augmented reality can be implemented using a see-through display.

Basic eye movement systems can be defined by their functional goals, the conditions under which they function, and the presumed distinct neuronal circuitry that forms them. Basic eye movement systems include such descriptions as saccadic, smooth pursuit, nystagmus, and vergence systems, which all act to bring a visual target of interest located on the fovea. The fixation, labyrinthine reflex, and optokinetic systems help to maintain steady fixation of a target when movement is present.

Biometrics means technologies or processes that measure and analyze human body characteristics, such as eye retinas and irises, and can be used for identity authentication. Physiologic based biometrics can include the characteristics of a person's unique physical vital signs and/or blood chemistry. Biometric sensors can measure normal or abnormal vital signs or chemical values. These values can be stored/used to evaluate a person's health.

A dongle is a hardware device attached to a computer without which a particular software program will not run. Dongles can be wireless adapters. They can be a device plugged into a USB port to enable wireless access from a computer to an external Wi-Fi device, to a mobile phone, to the internet via high-speed broadband, or to a printer or other peripheral. A dongle can be used to ensure that only authorized users can use a software application. When a program that comes with a dongle runs, it checks the dongle for verification as it is loading. If more than one application requires a dongle, multiple dongles using the same port can be daisy-chained.

Electroencephalography (EEG) is the measurement and recording of brain activity from special sensors in contact with the head. This procedure tracks and records brain wave patterns. An electroencephalograph measures voltage fluctuations resulting from ionic current flows within the neurons of the brain and show patterns of normal and abnormal brain electrical activity. There are several types of brain waves: Alpha waves have a frequency of 8 to 12 cycles per second. Alpha waves are present only in the waking state when your eyes are closed but you are mentally alert. Alpha waves go away when your eyes are open or you are concentrating. Beta waves have a frequency of 13 to 30 cycles per second. These waves are normally found when you are alert or have taken high doses of certain medicines, such as benzodiazepines. Delta waves have a frequency of less than 3 cycles per second. These waves are normally found only when you are asleep or in young children. Theta waves have a frequency of 4 to 7 cycles per second. These waves are normally found only when you are asleep or in young children. Abnormal patterns may result from conditions such as head trauma, stroke, brain tumor, or seizures. An example of an abnormal pattern is called "slowing" in which the rhythm of the brain waves can be slower than what would be expected for the patient's age and level of alertness.

Fixation is an active process that holds the eyes steady on the target. Eye movements can occur during normal fixations that are imperceptible to the human eye. These are microsaccades (very small amplitude saccades), microdrifts (smooth, meandering eye movements of a very slow velocity), and microtremor (rapid oscillations with amplitudes much smaller than microsaccades). Other normal-fixation eye movements include square wave jerks, which are perceptible to the human eye. They consist of a saccade away from the visual target, followed by a saccade that returns the eyes to the visual target after a brief intersaccadic interval. A frequency of four to six square wave jerks per minute can be normal. A rate greater than 15 per minute can be considered abnormal. Inappropriate disruptions or dysfunction within the pathways of the fixation eye movement system can cause nystagmus (sustained oscillations with two phases that either are both slow or have a slow and a fast phase), intermittent saccadic oscillations or saccadic intrusions, and sustained saccadic oscillations. The voluntary fixation of the visual system is directly related with the fovea, the central area of the retina, that provides high-resolution visual stimuli. In human vision, fixation movements register the target into the foveae to maximize perceptible details in the area of interest. Studies using orientation-sensing elements have documented the importance of fixation, particularly in monitoring and controlling the physiological effects of vertigo, motion sickness, motion intolerance, or spatial disorientation. When persons sense vection or perceived rotation, evidence shows that focusing on the vertex point of an artificial horizon stops or mitigates the vection or spinning sensation. Similarly, when a person is on a vessel experiencing pitch and roll, focusing on an artificial horizon or stable horizontal plane can mitigate or control motion sickness. Vertigo is more controllable with foveal fixation on a small point and motion sickness is more controllable by visualizing an artificial horizon or stable horizontal plane.

A Fourier transform converts arbitrary motion into a series of sinusoidal motions at various frequencies. This allows a graph of input motion and output motion as a function of time (i.e. in the time domain) to be converted into a graph that shows the gain and phase response plotted as a function of frequency (i.e. the response in the frequency domain). A Fourier transform can convert a comparison of random natural motion (linear and/or rotational) of the head and the eyes into information that shows the gain and phase response of the eyes to movement of the head.

Frequency means the number of cycles (typically rotational cycles) per second. Frequency is expressed in Hertz, which is abbreviated as Hz.

Gain means the measured ratio of eye movement velocity to head movement velocity. More specifically, for example, the "gain" of an eye reflex can be defined as the change in the eye angle divided by the change in the head angle during the head turn. The gain of the horizontal and vertical eye reflex is usually close to 1.0, but the gain of the torsional eye reflex (rotation around the line of sight) is generally low.

An immersive display is a display that feels three-dimensional to the user and therefore causes the user to feel as if they are part of the scene. VR, AR, MD, and synthetic environments can also be called immersive environments. An immersive display presents an artificial, interactive, computer-related scene or image into which a user can immerse themselves. Immersion into virtual reality is a perception of being physically present in a non-physical world. The perception is created by surrounding the user of the VR system in images, sound or other stimuli that provide an engrossing total environment.

Marginal reflex distance is the distance between the center of the pupillary light reflex and the upper eyelid margin with the eye in primary gaze.

Multi-dimensional (MD) environments, for purposes of this disclosure and any claims, are environments that include displays that can present a perspective of an image in two or more dimensions. Examples of displays that project in two or more dimensions include immersive displays such as those used by IMAX, virtual simulators, two-dimensional displays that use psychological depth cues (such as linear perspective, occlusion, shading, texture, and prior knowledge, etc), stereographic displays, multi-view displays (such as lenticular displays), volumetric displays, holographic displays, and so-called pseudo three-dimensional techniques such as on-stage telepresence, fog screens, or graphic waterfalls.

Nystagmus, or dancing eyes, is an involuntary oscillation of one or both eyes. Nystagmus is a term to describe fast, uncontrollable movements of the eyes that may be: (a) side-to-side (horizontal nystagmus); (b) up and down (vertical nystagmus), or (c) rotary (rotary or torsional nystagmus). Generally, the eyes move rapidly in one direction (fast phase or fast component) and slowly in another direction (slow phase or slow component). Depending on the cause, these movements may be in both eyes or in just one eye. People experiencing nystagmus usually have decreased vision and poor depth perception, although those born with nystagmus may not realize that their vision is poor. Those with acquired nystagmus may experience double vision or oscillopsia, or that objects in their visual space appear to move. An acquired nystagmus may be accompanied by other symptoms such dizziness, difficulty with balance, hearing loss, poor coordination, and numbness. There can be many causes of nystagmus including stimulation of the inner ear, visual stimulation, drugs, or abnormalities within the central nervous system. Nystagmus can be acquired later in life due to neurological dysfunction such as a head injury, multiple sclerosis or brain tumors. Some medications may cause nystagmus. When it occurs vertically (e.g. up and down nystagmus), the patient may describe a rolling of the vision in front of them. A change in the speed of the nystagmus leading to a decrease in vision can be related to stress, the person's emotional state, fatigue, the direction of view, or when one eye is covered. Persons with nystagmus may report problems with balance. Impairment to binocular vision can be common with early onset nystagmus and depth perception is indirectly impaired in many people. Acquired nystagmus may cause vertigo or dizziness from the sensation of motion in the visual field. Nystagmus may decrease when the eyes converge to read. Low vision specialists can add prisms to induce convergence artificially and thus reduce the nystagmus in some patients. Vestibular nystagmus can be induced during self-rotation. The inner ear contains motion detectors (vestibular labyrinth) that project to the vestibular nuclei and cerebellum. A vestibular nystagmus can also be induced by irrigating the ears with warm or cold water. Vestibular nystagmus is typically inhibited by visual fixation. It also typically follows Alexander's law (it becomes greater upon gaze in direction of the fast phases). Processes that increase gaze-evoked nystagmus, such as ingestion of sedating medications, increase the effects of Alexander's law. In persons with poor vision, fixation may be ineffective. Diseases affecting the visual system, such as retinal disorders causing visual loss, commonly lead to nystagmus because visual fixation is no longer possible.

The optokinetic reflex responds to slip of the image of the visual world on the retina and helps maintain the visual axes on target, and provide subjective information about rotation of the head in space at low frequencies of sustained head rotation (<1 Hz). Optokinetic nystagmus (OKN) is the eye movement elicited by the tracking of a moving field. OKN consists of a slow eye movement phase followed by a quick eye movement phase in the opposite direction. It can be induced when a person in constant motion views a stationary visual target, for example a passenger on a train looking out the window at the scenery passing by. Optokinetic function requires that the eyes perform certain motions with the greatest speed and accuracy, which is accomplished by version movements. The optostatic function, which regulates the position of the eyes relative to each other and to the coordinates of space, is subserved by the vergence movements.

Phase (or phase shift), in this disclosure and claims, is a measurement of the relationship between eye movement velocity and head movement velocity at a particular oscillation frequency of the head. More specifically, phase shift is an offset in the timing of eye movement relative to head motion at a specific rotational oscillation frequency. Phase is a parameter that describes the timing relationship between head movement and reflexive eye response. When the head and eyes are moving at exactly the same velocity in opposite directions, they are said to be exactly out of phase, or 180°. If the reflex eye movement leads the head movement, a phase lead is present, and if the compensatory eye movement trails the head movement, a phase lag is present.

Pitch is referred to as rotation about the side-to-side axis (also called the lateral axis or transverse axis), which by example, passes through an airplane from wing tip to wing tip. Pitch changes the vertical direction the airplane's nose is pointing. A pitch motion is described as an up or down movement of the body, like that of bending forward or backward.

Provocative environment for purposes of this disclosure and the appended claims can be defined as a setting that can cause a health related response by a person.

Ptosis (also known as Blepharoptosis) is an abnormal low-lying upper eyelid margin, partially covering the eye, with the eye in primary gaze. Normally, the upper lid covers 1.5 mm of the superior part of the cornea.

Refresh Rate refers to how fast the series of viewed images are updated. High refresh rates can reduce the visual lag between a series of images and decreasing the lag means there can be less of a chance of getting sick due to VIMS. It also means a more responsive visual experience. Versions of displays can refresh visualized images from 75 Hz to more than 250 Hz, particularly in virtual or stereoscopic display systems.

A retinal image is a projection of an object onto the retina of the eyes. If any torsion is made in an eye, for example in clockwise direction, then the retinal image of the object rotates by exactly the same amount, but in counterclockwise direction.

Roll is a rotation about a longitudinal (lengthwise front-to-back) axis that is perpendicular to gravity. The longitudinal axis, using the example of a plane, passes through the plane from nose to tail. In aircraft terminology, roll can also be called bank. When referring to the head, roll represents a rotation of the face about an axis perpendicular to the face. It can also be described as tilt of the head towards a shoulder.

Saccades are quick, simultaneous movements of both eyes in the same direction, controlled by the frontal lobe of the brain. Humans do not look at a scene in fixed steadiness, the eyes move around, locating interesting parts of the scene and building up a mental, three-dimensional map corresponding to the scene. When scanning the scene or reading these words right now, your eyes make jerky saccadic movements and your eyes stop several times, moving very quickly between each stop. We cannot consciously control the speed of movement during each saccade; the eyes move as fast as they can. One reason for the saccadic movement of the human eye can be that the central part of the retina (known as the fovea) plays a critical role in resolving objects. Some irregular drifts, movements, smaller than a saccade and larger than a microsaccade, subtend up to six minutes of arc. Even when looking intently at a single spot, the eyes drift. This ensures that individual photosensitive cells are continually stimulated. Without changing input, these cells would otherwise stop generating output. Microsaccades move the eye no more than a total of $0.2°$ in adult humans. Covert corrective saccades (during head motion) and corrective overt saccades (post head motion) are strong indicators of a significant vestibular deficit. Saccadic parameters and fixation durations also change with increasing sleepiness. The saccadic system controls fast eye movements to a target, and the smooth pursuit system controls eye movements to track a slowly moving target. Characteristics of saccades that can be evaluated and assessed for pathologic changes include accuracy, latency (or initiation), amplitude (or angular distance traveled), and velocity (or amplitude per unit of time).

Six degrees of freedom (6DoF) refers to the freedom of movement of a rigid body in three-dimensional space. An example of a system including six degree of freedom can be one with three degrees of translation and three degrees of rotation movement. The three degrees of translation are heaving (up and down), swaying (left and right), and surging (forward and backward). The three degrees of rotation are pitching (forward and backward), yawing (rotating left and right), and rolling (tilting side to side). Translational motion can also be described as movement of an object without a change in its orientation relative to a fixed point. Rotation can also be described as an object turning about an axis.

Smooth pursuit eye movements allow the eyes to closely follow a moving object. It is one of two ways that humans can voluntarily shift gaze, the other being saccadic eye movements. Smooth pursuit eye movements are what we use to keep our eyes on and follow a moving object. Smooth pursuit differs from the vestibulo-ocular reflex, which only occurs during movements of the head and serves to stabilize gaze on a stationary object.

Symmetry (and asymmetry), in this disclosure and claims, is a comparison of eye response or (reflex) in opposite directions. The words symmetry and asymmetry can be used interchangeably. Symmetry can be typically expressed as a percentage. For example, the horizontal symmetry (or asymmetry) can be expressed using the following equation:

$$\text{Symmetry} = 100 \times ((\text{Left velocity}) - (\text{Right velocity})) / ((\text{Left velocity}) + (\text{Right Velocity}))$$

Horizontal symmetry can be related to yaw of the eyes. The equation for vertical symmetry (or asymmetry) is the same as the above with the words "up" and down substituted for right and left. Vertical symmetry can be related to pitch of the eyes. Symmetry can also be measured for head rotation as viewed from the front (i.e. roll) and the associated roll (or torsion) of the eyes on a clockwise versus a counter-clockwise direction when viewed from the front. Symmetry can be typically evaluated at the same frequencies as gain and phase. It can be performed for one eye or both eyes. Symmetry can also be described as a comparison of the slow component of the nystagmus when rotated to the right compared with rotation to the left. Asymmetry can be present in some cases of unilateral vestibular hypo-function, as well as in other forms of vestibular dysfunction.

Synthetic environments are computer simulations that represents activities at a high level of realism, from simulation of theaters of war to factories and manufacturing processes. A synthetic environment can be:

(a) a synthetic natural environment that represents things occurring in nature such as climate, weather, terrain, oceans, living objects, space, etc;

(b) a synthetic human-made environment that represents human-made structures such as buildings, bridges, roads, etc; or (c) a synthetic psychological environment that represents psychological influences on individuals and/or groups based on demography and other cultural factors.

Torsion refers to the process of being rotated about an axis. As it relates to the eye movement, it means any rotation of the vertical corneal meridians (any line bisecting the cornea through its apex). Torsional eye movements can be defined in two different ways, namely as a rotation about the line of sight and as a rotation about an antero-posterior (forward-to-backward) axis that is fixed in the head. The most natural definition of a torsional eye movement is as a rotation about the line of sight. The line of sight is the imaginary line that connects the eye with the fixation target. When the eye rotates about this line, the eyes remain fixated on this same target. When the eye makes any horizontal and/or vertical gaze shift, the line of sight and, therefore, the axis of rotation for torsion, shifts as well. For example, if one looks straight ahead, eye torsion occurs about an antero-posterior (forward-to-backward) axis. If one looks leftward, the axis of rotation for eye torsion is also rotated leftward.

Vection can be defined as a sensory-spatial illusion that creates false sensations of self-motion, in either linear or angular directions.

Vergence is the simultaneous movement of both eyes in opposite directions to obtain or maintain singular binocular vision. The interaction between vision and motor control allows us to develop an active sensor that achieves high accuracy of the disparity computation around the fixation point, and fast reaction time for the vergence control. Characteristics of vergence eye movements include velocity, latency, and waveform or trajectory. Waveform is the pattern of velocity change during a vergence movement Version is the rotation of the eyes about the vertical axis to maintain a constant disparity. Meanwhile, tilt is the rotation of each eye with respect to the horizontal axis. Finally, vergence is the rotation of each eye about the vertical axis to change the disparity.

Virtual reality (VR) can be defined as a computer-generated simulation of a three-dimensional image or environment that can be explored and interacted with by a user. The user becomes part of the virtual scene or immersed within the environment. While being part of the virtual environment, he or she can interact within a seemingly real or physical way, to use or manipulate objects or special electronic equipment. An example would be to perform a series of actions with a device or use a glove fitted with sensors or to wear a helmet with a projected virtual screen inside. Virtual reality environments are typically implemented stereoscopically. The display system for virtual reality can be an opaque display system, i.e. the user only sees the virtual scene and cannot see through the scene. The peripheral vision can be blocked to decrease any distraction from the user experience. Virtual reality can be used in simulators. Virtual display images may be actively streamed from an attached computer, a wireless computer source or from iOS or Android smartphones, smart display pads or directly with digital camera systems and virtual camera systems.

Visual acuity (VA) refers to clearness of vision, which can be dependent on optical and neural factors, i.e., (i) the sharpness of the retinal focus within the eye, (ii) the intactness and functioning of the retina, and (iii) the sensitivity of the interpretative faculty of the brain. A Snellen chart (eye chart that uses block letters arranged in rows of various sizes) is frequently used for visual acuity testing and measures the resolving power of the eye, particularly with its ability to distinguish letters and numbers at a given distance as well as distinguish letters and numbers at a given distance as well as the sharpness or clearness of vision.

Yaw is rotation around the vertical axis. A yaw motion of the head can be described as a horizontal movement of the face from side to side. When turning the head horizontally or vertically (i.e., yaw or pitch) the vestibulo-ocular reflex (VOR) maintains visual fixation on the object of interest throughout the head movement and thereby reduces the motion of the image on the retina.

3. EYE TRACKING

Eye tracking means measuring either the point of gaze (where one is looking) or the motion of an eye relative to the head. Embodiments of the present invention can use video cameras that look at all or part of the eye or eyes. They can use programs to process the images taken from the video cameras to look for abnormal eye movements, such as saccades, nystagmus, or other forms of abnormal twitching, which can indicate an unhealthy physical response to a provocative environment, such as those listed previously in this disclosure. The eye tracking system (or videonystagmometry system) could detect vertical, horizontal, and/or torsional nystagmus. These abnormal measured responses can be used to diagnose pathology and can be sent to an external device or vehicle. Eye tracking data can be used in real time or logged. Eye tracking can be beneficial in predicting human performance and evaluating physical disorders. Eye measurement in a VR, AR, MD, or synthetic environment can assess recovery progress and return to play or occupational activities.

The eye tracking system can be used with or without a light source. The light source can be infrared and can be directed toward the eye or eyes. The camera can be used to track the reflection of the light source and visible ocular features such as the iris, pupil, cornea, and sclera. The data from the eye tracking system can be used to measure the movement features of the eyes, position or rotation of the eye, velocity of the eye movement, and the direction of gaze. Additional information such as pupil diameter can also be detected by the eye tracker. Aggregated eye tracker data can be written to a file for later analysis. Eye tracker data can be used to analyze the visual path of one or more participants across an interface such as a computer screen. In this case, each eye data observation can be translated into a set of pixel coordinates. From there, the presence or absence of eye data points in different screen areas can be examined. This type of analysis can be used to determine which features are seen, when a particular feature captures attention, how quickly the eye moves, what content is overlooked and virtually any other gaze-related question. Graphics are often generated to visualize such findings. In a variant, eye position can be extracted from video images. In another variant search based on an electro-oculogram may be used. When using a video-based eye tracker, the camera can be focused on one or both eyes and used to record eye movement as a viewer looks at some kind of stimulus. In one embodiment, the eye-tracker uses the center of the pupil and infrared and/or near-infrared non-collimated light to create corneal reflections (CR). The vector between the pupil center and the corneal reflections can be used to compute the point of regard on surface or the gaze direction. A simple calibration procedure of the individual is usually needed before using the eye tracker of this embodiment.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. Bright pupil techniques are not effective for tracking outdoors as extraneous infrared sources interfere with monitoring. In embodiments of the present invention, eye tracking might use a sampling rate of at least 30 Hz. Typical sampling frequencies include 50 Hz, 150 Hz, 250 Hz, 350 Hz, 1000 Hz, and 1250 Hz, with the majority being 250-350 Hz. The higher sampling frequencies are needed to capture the detail of the very rapid eye movement during reading, when used for entertainment purposes, or in VR, AR, MD, or synthetic environments.

Eye movement information from the eye tracker typically comprises fixations and saccades. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus were processed during an eye tracking session. On average embodiments of the present invention are designed to accurately capture fixations that last for around 200 ms during the reading of linguistic text and 350 ms during the viewing of a scene. Preparing a saccade towards a new goal takes around 200 ms.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. In one embodiment, the software can then generate data about these actions in the form of heat maps and saccade pathways. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

One attractive capability of the eye tracking technology disclosed here can be eye movement analysis, which can provide valuable insight into users' overt visual behavior and attention. Note that, without further analysis, raw eye tracking data is practically useless. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades, and smooth pursuits. Fixations are a result of one's desire to maintain gaze on a specific, stationary object. Smooth pursuits are similar except for the object of interest in motion. Saccades represent a voluntary shift of focus from one fixation point to another.

In embodiments of the present invention, saccades can be detected by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it can be more suitable for real-time applications.

Beyond the analysis of visual attention, eye data can be examined to measure the cognitive state and workload of a participant. Some techniques have been validated in multiple contexts as a reliable indicator of mental effort. Situations in which this type of analysis of visual attention can be useful include: operating a vehicle, reading a magazine, surfing the interne, searching the aisles of a grocery store, playing a video game, watching a movie, looking at pictures on a mobile device, and viewing images in a VR, AR, MD, or synthetic environment. With few exceptions, anything with a visual component can be eye tracked. People use their eyes almost constantly, and understanding how the eyes are used has become an extremely important consideration in research and design.

Some of the techniques for tracking the eye include: limbus tracking, pupil tracking, Purkinje image tracking, corneal and pupil reflection relationship tracking, and corneal reflection and eye image tracking using an artificial neural network. Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still or the apparatus must be fixed to the user's head. Due to the occasional covering of the top and bottom of the limbus by the eyelids, it can be more helpful for precise horizontal tracking only.

Regarding pupil tracking, this technique can be similar to limbus tracking. The difference is that in pupil tracking the smaller boundary between the pupil and the iris is used instead of the boundary between the white sclera and the dark iris. Once again, the apparatus must be held completely still in relation to the head. The advantage of this technique over limbus tracking is that the pupil can be far less covered by the eyelids than the limbus. Thus, vertical tracking can be accomplished in more cases. Additionally, the border of the pupil can be often sharper than that of the limbus, which yields a higher resolution. The disadvantage of pupil tracking is that the difference in contrast is lower between the pupil and iris than between the iris and sclera, thus making border detection more difficult.

Regarding Purkinje image tracking, when (infrared) light is shone into the user's eye, several reflections occur on the boundaries of the lens and cornea. These reflections are called Purkinje images. The first Purkinje image is also called the glint, and this together with the reflection of light off the retina—the so-called bright-eye—can be video-recorded using an infrared sensitive camera as a very bright spot and a less bright disc, respectively. When the eye is panned horizontally or vertically, the relative positioning of the glint and the center of the bright-eye change accordingly, and the direction of gaze can be calculated from these relative positions.

Regarding pupil and pupil reflection relationship tracking, eye trackers can combine a camera with an infrared light source that illuminates the eye with bursts of invisible infrared light. Some of this infrared light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infrared light, which can be picked up by the camera. By analyzing the reflections, it is then possible to determine where the eye is pointing. Because eyes move in tandem, this only needs to be done for one eye, unless more thorough eye measures are used for other applications in the virtual system, such as the vestibular ocular reflex. The technique is able to cope with blinking, head movements, dim light, glasses and contact lenses.

The use of artificial neural networks (ANNs) for computation is a more recently developed technique. The raw material for eye-gaze tracking is still a digitized video image of the user, but this technique is based on a more wide-angled image of the user, so that the entire head can be in the field of view of the camera. A stationary light can be placed in front of the user, and the system starts by finding the right eye of the user by searching the video image for the reflection of this light—the glint, distinguished by being a small, very bright point surrounded by a darker region. It then extracts a smaller, rectangular part of the video image (typically only 40 by 15 pixels) centered at the glint, and feeds this to an ANN. The output of the ANN can be a set of display coordinates. The ANN requires more than the simple calibration that is required by the other techniques; it must be trained by gathering images of the user's eye and head for at least three minutes while the user visually tracks a moving cursor on the display. This can be followed by an automatic training session that uses the stored images lasting approximately 30 minutes using the current technology, but then the system should not require re-calibration on the next encounter. To improve the accuracy of an ANN-based system, the corneal/pupil-based calculations can be augmented with a calculation based on the position of the glint in the eye socket. The great advantage of ANN-based techniques is that due to the wide angle of the base image, user head mobility can be increased.

4. EYELID TRACKING

The eyelid (singularly called the palpebral and both eyelids are called palpebrae) refers to two folds of skin and muscle that can be closed over the exposed portion of the eyeball. The opening between the lids is called the palpebral aperture or palpebral fissure. The palpebral fissure is the elliptic space between the medial and lateral canthi of the two open eyelids (e.g. the longitudinal opening between the eyelids). In adults, this measures about 9-12 mm vertically. It can be also referred as the height or distance of the palpebrae fissure (PF) between the upper and lower eyelid margins at the axis of the pupil for which the normal measurement is 9-12 mm. The configuration varies with a person's physical characteristics and race. The range of eyelid or palpebral movement from full elevation to closure ('eyelid excursion') is usually greater than 10 mm. This range can easily be measured. It forms an important part of the assessment of any individual with ptosis. Fatigability can be assessed by detecting any lowering of the eyelid during sustained upgaze for at least 60 seconds. Ptosis (or lowering of the upper palpebral position) is present when the upper eyelid is less than 2 mm from mid-pupil. Reduction of the upper field of vision to 30 degrees or less is present in 97% of eyes with ptosis so defined. In drooping, the vertical height of palpebral fissure (normally near 10 mm in adults) would decrease. Subtracting the drooping from the normal height in the other eye give the amount of the drooping in which: mild ptosis=2 mm: moderate ptosis=3 mm; and severe ptosis=4 mm.

As previously noted, embodiments of the present invention can use a camera to detect eyelid behavior such as eyelid (palpebral) closure, eyelid position, blinking, eye muscle movement, eye closure rate, eye closure duration, palpebral fissure height, palpebral aperture, marginal reflex distance, frequency of eye closure, velocity of eye closure, abnormal eye response, and/or abnormal eye reflexes. The eye sensor can measure the data in either one eye or both eyes. Embodiments of the present invention can then use this information to detect and respond to abnormalities. These eyelid behaviors can be indicative of unhealthy physical responses, such as those listed previously in this disclosure. These abnormal measured responses can be used to diagnose pathology and can be sent to an external device or vehicle.

A typical person makes 3-5 eye movements per second, and these movements are crucial in helping us deal with the vast amounts of information we encounter in our everyday lives. Spontaneous eye blinking serves a critical physiological function, but it also interrupts incoming visual information. This tradeoff suggests that the inhibition of eye blinks might constitute an adaptive reaction to minimize the loss of visual information, particularly information that a viewer perceives to be important. From the standpoint of physiology, blinks exist primarily to protect: They keep the eyes hydrated and protect against foreign objects. When the blinking process starts, the eye moves around 2° in the inferior nasal-ward direction while it performs a cyclo-torsional rotation. Simultaneously with these movements, the eye performs a retraction inside the orbit of 0.5-1.5 mm.

Average individual rates of blinking increase with age and are correlated with dopamine levels in humans. However, blinking also relates, like other autonomic processes (e.g., heart rate, perspiration), to cognitive states beyond physiological function alone. Blink rate has been observed to vary as a function of several cognitive tasks, and blink rates decrease during activities that require greater attention, as when reading vs. sitting in a waiting room. Studies have also shown that the timing of blinks can be related to both explicit and implicit attentional pauses in task content. Together, these observations highlight a key difference between blinking and other autonomic reactions.

Blinking sets a physical limit on visual attention because of its profound interruption of incoming visual information. Generally, humans blink at least about 5-30 times per minute or about 7,000-43,000 times per day. The typical duration of palpebrae closure can be also variable during blinks, lasting 40 to 300 milliseconds. Each involuntary-reflexive blink generally averages about 250 milliseconds. This amounts to about 1,750-10,800 seconds per day of eye closure due to involuntary blinking. As tiredness or sleepiness occurs, the eye blinks may get longer and slower and/or the blink rate may vary, and/or the eyelids (e.g. palpebrae) may begin to droop with small amplitude eye lid blinks, e.g., until the eyes begin to close for short term "microsleeps," (i.e., sleep conditions that last for about 3-5 seconds or longer, or for prolonged sleep). Many other factors affect the duration of palpebral closure, such as drugs, alcohol, and medical conditions. Even individuals who have dry eyes can have a longer eye-blink duration. People with dry eyes can have a median extended blink duration of more than 2 times longer than that of normal.

Eye blinks are typically classified into three categories: spontaneous eye blinks (which occur frequently); reflexive eye blinks which are evoked by an external stimulus; and voluntary eye blinks, caused by intentional eye closing. Embodiments of the present invention can be used to identify and analyze these three types of blinks to discriminate between normal blinks and those associated with a condition indicative of spatial disorientation, drowsiness, inattentiveness or other kinds of performance impairment.

Ocular indices related to eye blinks can include blink rate, blink duration, blink amplitude, percentage of eyelid closure, eyelid closing/opening speed or ratios of these indices. These ocular indices have the potential to be recorded by monitors that can warn vehicle drivers (or pilots), or any individual operating a device, if they are approaching a sleepiness threshold. One advantage of ocular indices can be that they can be recorded via non-contact methods such as video or infrared reflectance oculography. One ocular index that has been shown to be effective as a measure of sleepiness can be blink rate. Increased rate of blinking has been associated with increases in sleepiness. For instance, examinations of sleep-deprived individuals reveal positive correlations between blink rate and the amount of time spent awake. Moreover, subjective sleepiness has been positively correlated with time spent awake. Blink rates have also been found to increase during a 40-minute daytime vigilance task. Increases in blinking rates have an association with increases in sleepiness. The duration of eyelid closure (i.e. blink duration) can also be a sensitive measure of sleepiness. Blink frequency and duration have been associated with the performance of other attentional tasks (e.g., driving, piloting aircraft) and correlate with subjective sleepiness scales and electroencephalographic changes. Suppression or reduction of blinking occurs with tasks that have a high visual attention demand, such as reading. Blink duration correlates with increased sleepiness or fatigue and may provide a more significant index for alertness than blink frequency. Normal blink frequency is on the order of 9 to 13 per minute in the daytime, increasing to 20 to 30 per minute in sleep-deprived subjects or patients with abnormal sleep patterns. Regarding oculomotor parameters, blink duration, delay of lid reopening, blink interval and standardized lid closure speed were identified as the best indicators of subjective as well as objective sleepiness. All of the features associated with eyelid tracking can be measured and used in VR, AR, MD, and synthetic environments.

5. DESCRIPTION OF THE FIGURES

Referring now to the figures, FIG. 1 illustrates an aircraft cockpit 100, which is an exemplar environment that can be provocative to motion sickness and spatial disorientation. In the environment shown, a pilot 110 is equipped with a flight suit 112 and a helmet 114. The helmet 114 may include a display 116. The pilot 110 is also equipped with various sensors, 130 and 132, which monitor one or more physiologic and/or environmental parameters. There can be any quantity of sensors and the sensors, 130 and 132, may include any of the sensors described in this disclosure or any other sensor capable of being understood by anyone skilled in the art. The sensors, 130 and 132, could be attached to the pilot. The sensors, 130 and 132, could be in any other location that could provide useful information. The output of the sensors, 130 and 132, is typically directly or indirectly input into the electronics or avionics 200. The electronics may include central processors system(s) and sensor interfaces (not shown separately). In the configuration shown, the pilot 110 can interact with a console 118 that provides the pilot 110 with the means to visually and haptically interface with the aircraft avionics and electronics to access information and to control the aircraft. In the configuration shown, the pilot 110 is seated in a seat 140 that can be part of a cockpit structure 142. The cockpit structure 142 may be set with rockets 144 or charges for emergency ejection from the aircraft cockpit 100. Note that it is possible to have more than one pilot 110 (e.g. a pilot and co-pilot or a trainee and instructor) in such an environment 100 and that the environment 100 can be any vehicle, simulator, or device capable of being understood by anyone skilled in the art. Note also that the display 116 could be helmet mounted, the display 116 could be eyewear mounted, the display 116 could be attached to another type of head-attachable unit, or the display could be in a location not attached to the pilot 110 or other user of the embodiments described herein.

Figure 2:
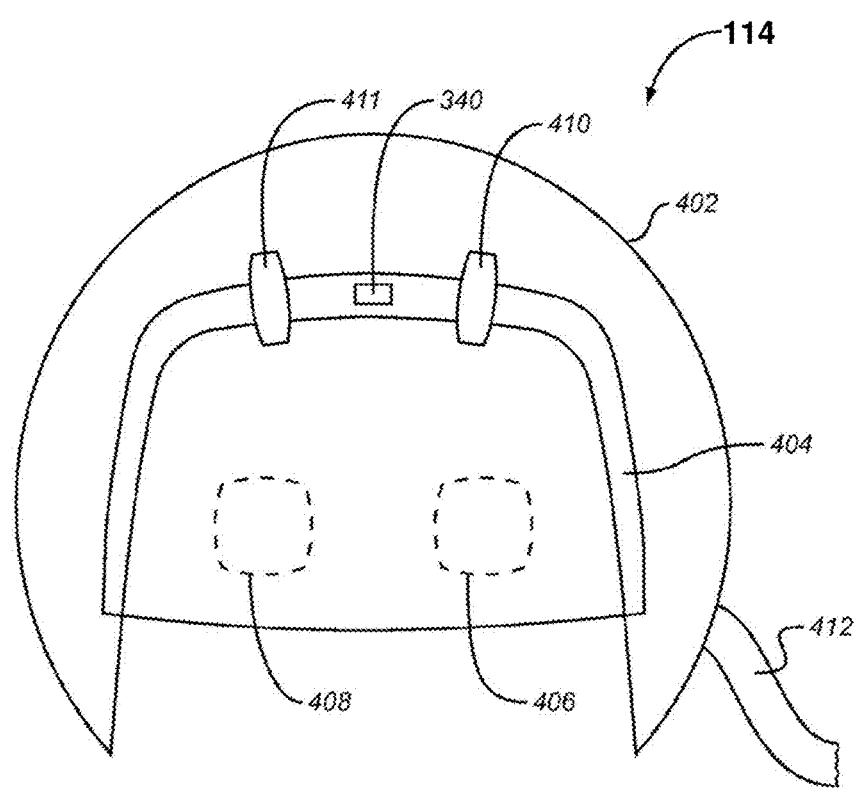
FIG. 2 illustrates a helmet with a display, eye sensors, and a head tracker.

FIG. 2 illustrates more detail of the helmet 114 that was also shown in FIG. 1. The helmet 114 has a visor 404 onto which data can be displayed in display regions, 406 and 408, that are analogous to the display 116 shown in FIG. 1. The helmet 114 is also configured with eye sensors 410 and 411 that measure ocular (eye and eyelid) parameters such as those described in other parts of this disclosure. The helmet 114 can include a head tracker 340, for measuring head orientation and other measures of head orientation and position as described in this disclosure. The eye sensors 410 and 411, and the head tracker 340 can be connected to the other avionics systems and subsystems via an umbilical 412 that contains electrical and optical conduits (not shown) for communication. The helmet 114 can include a helmet shell 402 that attaches to the pilot's head (not shown). The visor 404, eye sensors 410 and 411, and umbilical 412 can be attached to the helmet shell 402.

Figure 3:
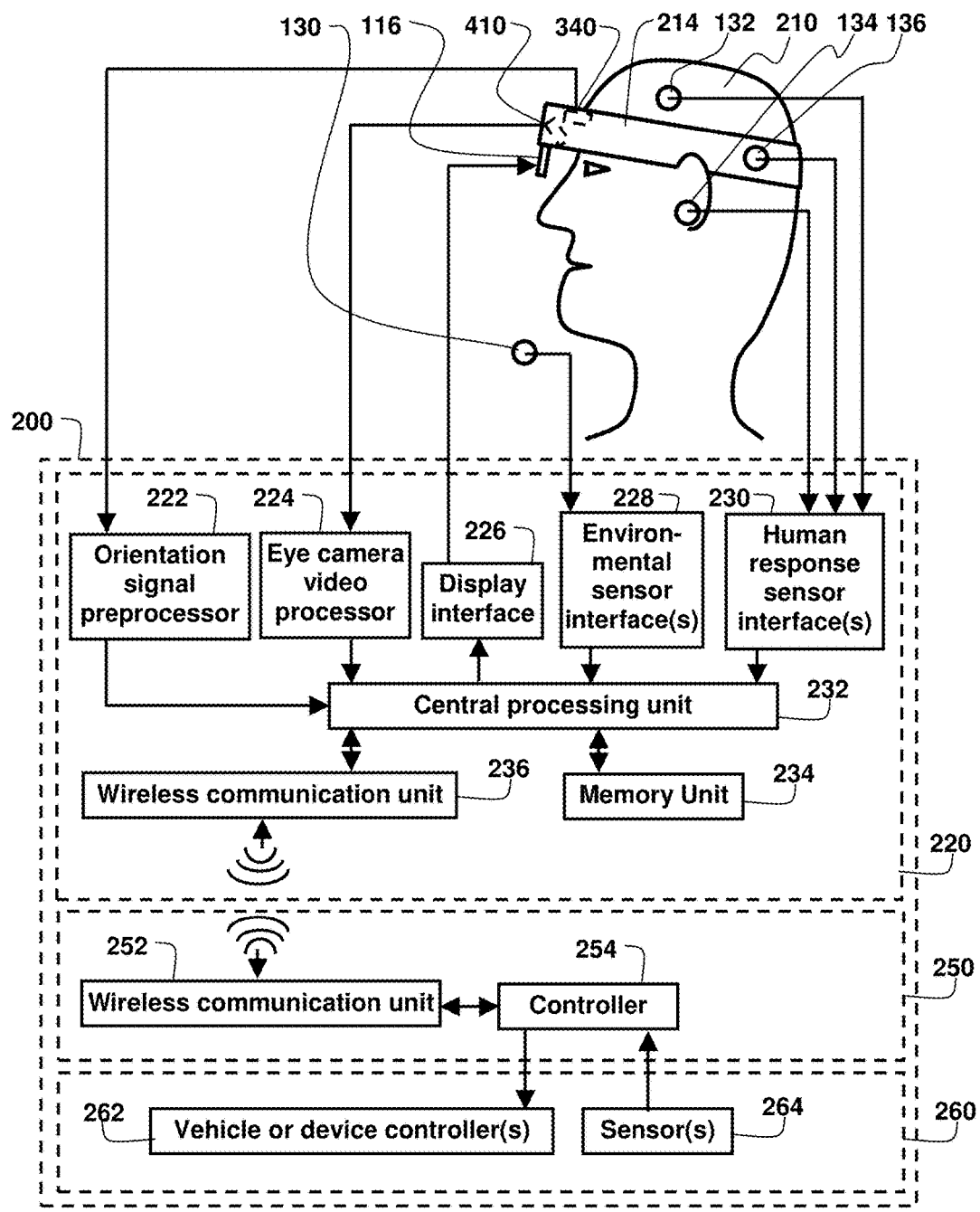
FIG. 3 illustrates a wireless system for controlling a vehicle or device in response to measured unhealthy human response to a provocative environment.
Figure 4:
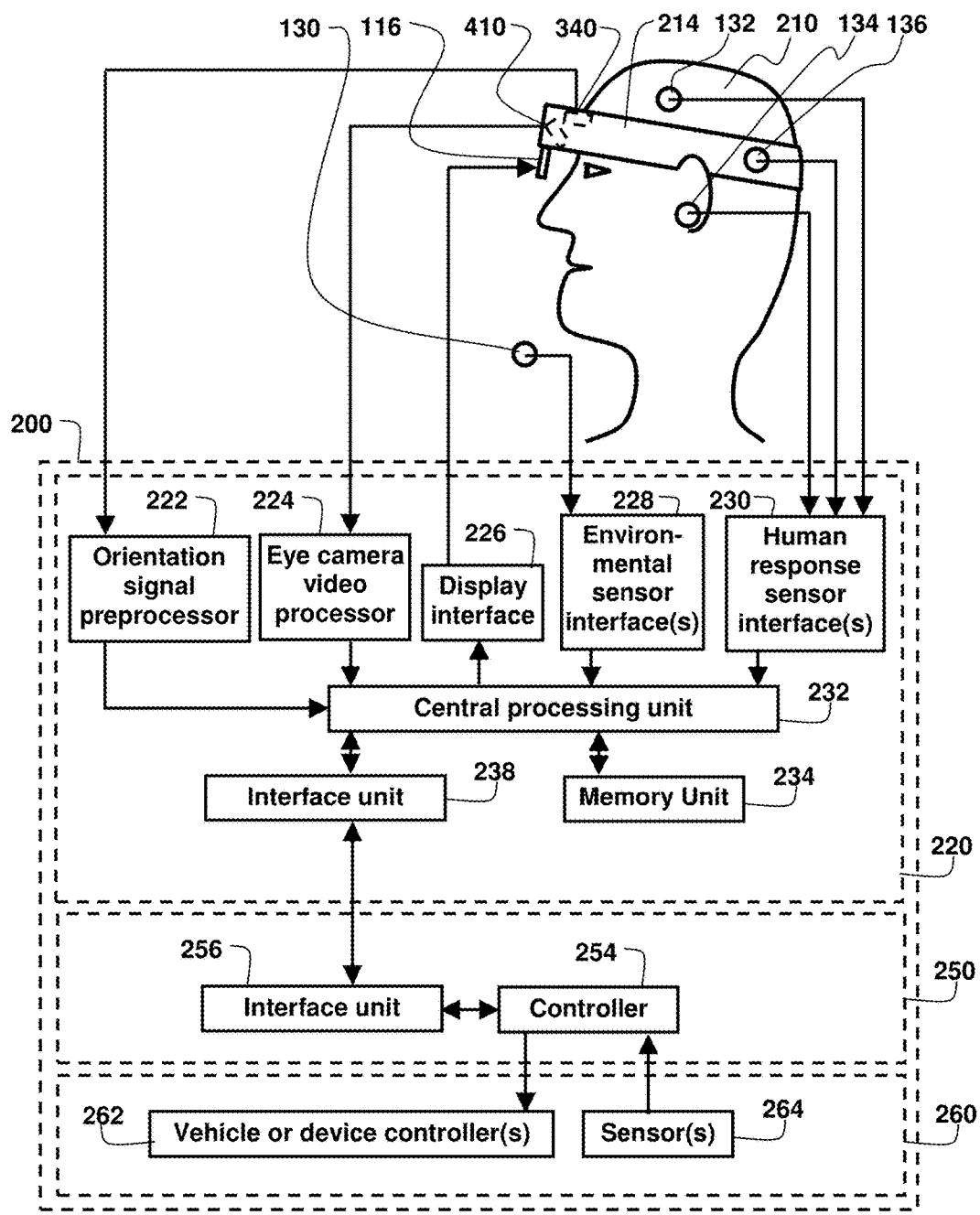
FIG. 4 illustrates a wired embodiment of a system similar to that shown in FIG. 3.

FIG. 3 illustrates an embodiment of a wireless system for controlling a vehicle or device in response to a measured unhealthy human response to a provocative environment. FIG. 4 illustrates an embodiment of a wired system for controlling a vehicle or device in response to a measured unhealthy human response to a provocative environment. Parts of the embodiments shown in FIG. 3 and FIG. 4 are similar to what was illustrated in FIG. 1 and FIG. 2, but displayed more generically. Referring to FIG. 3 and FIG. 4, the user 210, is a more generic representation of the pilot 110, of FIG. 1. The user 210 is wearing a head-worn unit 214, which is a generic form of the helmet shown at 114 in FIG. 1 and FIG. 2. The head-worn unit 214 could be a helmet, it could be a head band, it could be a cap or hat, it could be eyeglasses, it could be a visor, it could be a unit attached to another head-worn device, it could be any other head-worn item capable of being understood by anyone skilled in the art. The head worn unit 214 can include a display 116, which can be similar to the display 116 in FIG. 1 and the display regions 406 and 408 in FIG. 2. The head-worn unit 214 can include a head tracker 340 as described with reference to FIG. 2 and in other parts of this disclosure. The head-worn unit can include one or more eye sensors 410, which can be similar to the eye sensors 410 and 411 in FIG. 2. There can be one or more environmental sensors, an example of which is shown at 130. This environmental sensor was also shown at 130 in FIG. 1. The environmental sensor 130 or sensors can be any type of sensor, including any of those described in other parts of this disclosure. The environmental sensor 130 or sensors can measure any environmental factor or parameter, including any of those described in other parts of this disclosure. The environmental sensor 130 or sensors can be located on the head-worn unit, on the user's head, on another part of the user's body, on something that is attached to any part of the user's head or body, on a vehicle or device, or in any location that gives an environmental reading and is capable of being understood by anyone skilled in the art. There can be one or more human response sensors 132 and 134, an example of which was also shown at 132 in FIG. 1. The human response sensor or sensors, 132 and 134, can measure any physical or physiologic factors, parameters, or indicators associated with the user 210, such as any of those described in other parts of this disclosure. The human response sensor or sensors, 132 and 134, can be any type of sensor, including any of those described in other parts of this disclosure. The human response sensor or sensors, 132 and 134, can be located on the head-worn unit, on the user's head, on another part of the user's body, on something that is attached to any part of the user's head or body, on a vehicle or device, or in any location that gives a measurement of the user and is capable of being understood by anyone skilled in the art.

Further referring to FIG. 3 and FIG. 4, the electronics or avionics are shown at 200 and are a more detailed representation of what was shown at 200 in FIG. 1. The electronics can be divided into a local electronic device 220, a remote electronic device 250, and an external device or vehicle 260. The local device 220 could be part of the head-worn unit, it could be worn on a part of the user's 210 body, or it could be located somewhere proximate to the user, such as in the airplane. In the embodiment shown in FIG. 3 and FIG. 4, the local device 220 comprises an orientation signal preprocessor 222, an eye camera video processor 224, a display interface 226, on or more environmental sensor interfaces 228, or more human response sensor interfaces 230, a central processing unit 232, a memory unit 234, and a wireless communication unit 236. In the embodiment shown in FIG. 3, the remote electronic device 250 comprises a wireless communication unit 252 and a controller 254 and the external device or vehicle 260 comprises one or more vehicle/device controllers 262 and sensor(s) 264.

Referring in further detail to FIG. 3 and FIG. 4, the orientation signal preprocessor 222 takes orientation signals from the head tracker 340, the eye camera video processor 224 takes input from the eye sensor 410, the display interface 226 sends a display signal to the display 116, the environmental sensor interface(s) 228 receive signals from the environmental sensor or sensors 130, and the human response sensor interface(s) 230 receive signals from the human response sensor(s) 132 and 134. Communication between the various sensors (eye tracker, environmental sensors, human response sensors), the display, and the various preprocessors, processors or interfaces can be wired communication or wireless communication. If the communication is wireless, it can use any protocol and technology capable of being understood by anyone skilled in the art such as WiFi (examples of which include IEEE 802.11b/g/n/ac), WiMax, a cellphone signal (2G, 3G, 4G, CDMA, EVDO, GSM/GPRS, LTE), Zigbee, WLAN, Bluetooth, optical wireless (infrared, laser, etc), near field communications, sonar, ultrasonic, etc. Alternatively, the wireless communication can comprise a wireless local area network (WLAN). The wireless communication may be direct, such as using an infrared link, Bluetooth, near field communication, or ZigBee. The wireless communication could use include an interface for "off-the-grid" networks (such are FireChat) where there is not cellular phone service or no internet connection. Further referring to the embodiments shown in FIG. 3 and FIG. 4, each of the preprocessors, processors or interfaces can be connected to the central processing unit 232, which can be a digital microprocessor that interacts with the memory unit 234 to store and analyze data.

The difference between the embodiment shown in FIG. 3 and the embodiment shown in FIG. 4 is that the embodiment in FIG. 3 has a wireless connection between the local electronic device 220 and the remote electronic device 250 and the embodiment in FIG. 4 has a wired connection between the two electronic devices 220 and 250. Referring to the embodiment shown in FIG. 3, a wireless communication unit 236, that is connected to the central processing unit 232 of the local electronic device, transmits and/or receives data with a wireless communication unit 252 that is connected to the controller 254 of the remote electronic device 250. This wireless communication can use any protocol and technology capable of being understood by anyone skilled in the art, such as the technologies described in other parts of this disclosure. In the embodiment shown in FIG. 4 an interface unit 238, that is connected to the central processing unit 232 of the local electronic device 220, transmits and/or receives data with an interface unit 256 that is connected to the controller 254 of the remote electronic device 250.

In addition to the elements shown in FIG. 3 and FIG. 4, the local electronic device 220, the remote electronic device 250, and/or the vehicle or device 260 could also have the following attributes:

a. The local electronic device 220, the remote electronic device 250, and/or the vehicle controller 260 could comprise a battery and/or a power management circuit. The power management circuit could communicate with the central processing unit 232. The power management circuitry could receive power from a charging port and manage and distributes power to charge the battery and for use by any components requiring electric power. The power circuitry could be connected to status display circuitry. The status display circuitry could communicate with the central processing unit 232.

b. The local electronic device 220, the remote electronic device 250, and/or the vehicle controller 260 could comprise a dongle, which could further include its own communications circuitry and logic circuitry or use the central processing unit 232.

c. The local electronic device 220, the remote electronic device 250, and/or the vehicle controller 260 could be connected by an umbilical connection (412 in FIG. 2).

d. The central processing unit 232 can use firmware programs and these programs could be stored in the memory unit 234. Data can be stored in the computer-readable memory unit 234 for later retrieval.

e. The data can provide an alarm to the operator or to others. The alarm can be local or remote. The alarm and any responses can be done in real time, or using active live streaming. The alarm can be auditory, haptic, or visual. The auditory alarm can be a variety of types with varied frequencies. The auditory device can be attached to the head worn system, the operator's skin, or it can be in contact with the skin surface by being affixed to something in contact with the skin surface, or it can be nearby in audio range. The haptic alarm can be in the form of a sensor that vibrates, stimulates, pulsates, twitches, provides a sense of movement, or sends an alternating electric current to the skin causing a somatosensory experience to the user or operator. The haptic device can be attached to the head worn display, attached to the skin surface, or it can be in contact with the skin surface by being affixed by what is being worn or touched or in close enough range to produce a somatosensory experience. The remote location can alternatively, or additionally, send a somatosensory experience back to the user or operator, or the remote location could send an auditory or visual signal back to the user or operator. The visual alarm can be in the form of lights, which may have different colors, text information or other visual symbology.

f. The local electronic device 220, the remote electronic device 250, and/or the vehicle controller 260 could be implemented on a single circuit board for all three devices. Each device could be implemented on a separate circuit board. A device could be implemented on more than one circuit board. The system could be implemented in any circuitry configuration capable of being understood by anyone skilled in the art.

g. The sensors (such as those shown at 340, 410, 130, 132, 134, and 136 in FIG. 3 and FIG. 4) can include micro-electro-mechanical system (MEMS) chip(s) (sometimes referred to as micromachines and can take the form of NEMS (nano-electro-mechanical systems). Embodiments can use two chips, which sense inertial changes and together provide six degrees of freedom: three degrees representing rotation on three orthogonal axes and three representing inertial changes along each of the three axes. For some applications, only two or three degrees of freedom may be required to gather and track the necessary data to generate the symbology, the most important being pitch and roll.

h. The sensors (such as those shown at 340, 410, 130, 132, 134, and 136 in FIG. 3 and FIG. 4) can use pre-processing circuitry to clean up the signal prior to connecting to interface circuitry.

i. Embodiments of the head worn system or method can include capabilities that allow the user to interact with a VR, AR, MD, or synthetic environment either through the use of standard input devices such as a keyboard, and mouse, or through multimodal devices such as a wired glove. These input devices can be operated using haptic methods, sound, or movements of the body.

j. Sensors in contact with the user's skin and affixed to the user worn VR, AR, MD, or synthetic environment can provide a display to the user and/or to a remote site, such as to a physician. This can evaluate the user's physiologic response to certain stimulus situations or when participating in physical activities while using the immersive system.

k. The system can include or be coupled to other peripherals, such as a touchpad, an integrated microphone, a high definition (HD) camera, a speaker, and/or an electronic device such as a smart phone, a smart watch, a portable computer, or any wearable computing device.

Figure 5:
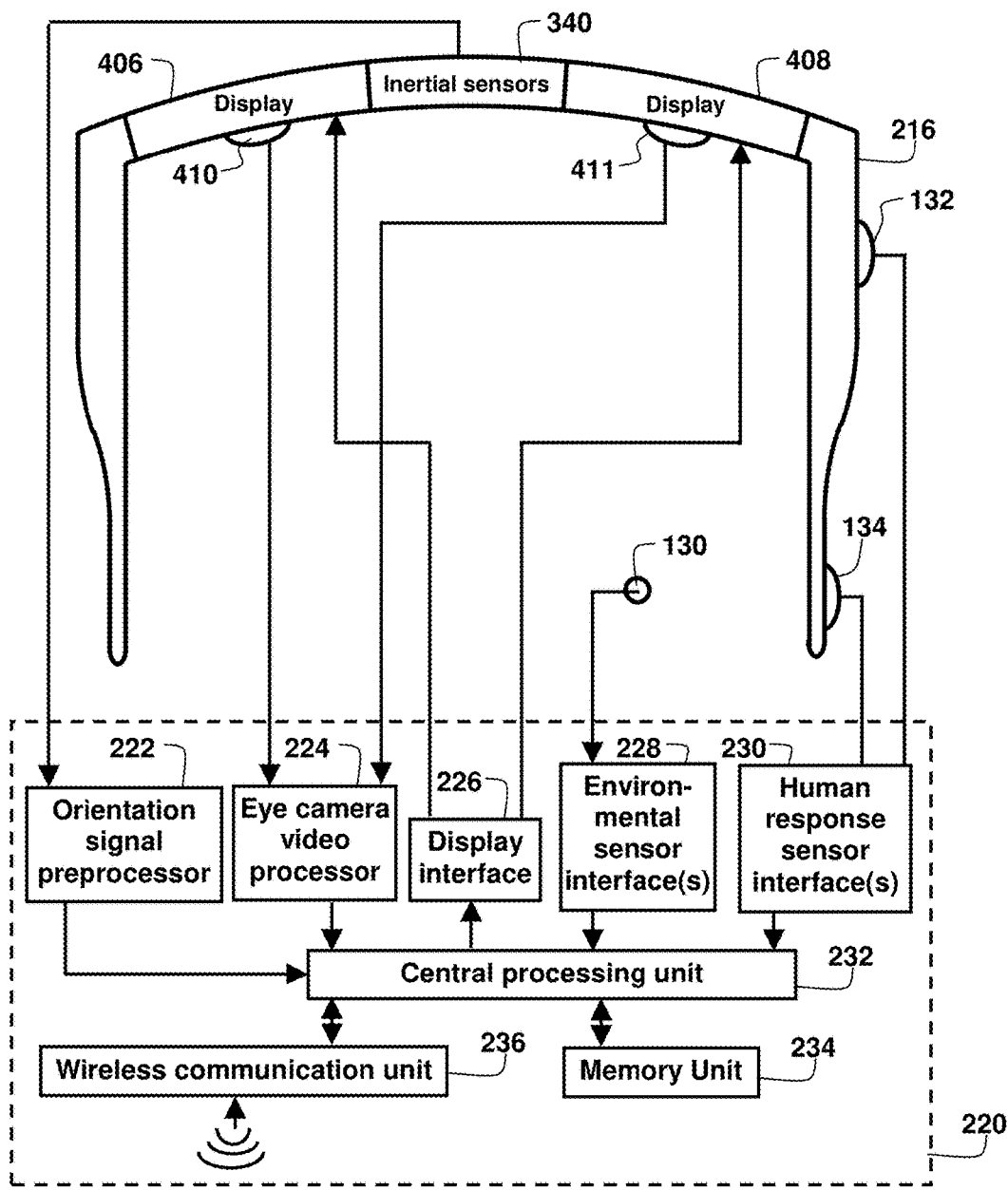
FIG. 5 provides another illustration of an embodiment similar to FIG. 3 and FIG. 4.

FIG. 5 provides another illustration of an embodiment similar to FIG. 2, FIG. 3, and FIG. 4. Referring to FIG. 5, the head worn unit of FIG. 3 and FIG. 4 is a head worn set of eyewear glasses (spectacles) or a goggle, shown at 216. The head worn eyewear unit 216 includes two display regions 406 and 408 that are similar to the display regions 406 and 408 in FIG. 2. The head worn eyewear unit 216 includes a head tracker 340, which comprises inertial sensors. The unit 216 has two eye trackers 410 and 411 that are similar to what was shown in FIG. 2, FIG. 3, and FIG. 4. Note that these eye trackers (or eye sensors) could also be eyelid trackers (or eyelid sensors). There can be one or more environmental sensors, such as that shown at 130. There can be one or more human response sensors 132 and 134. The sensors, display, and trackers can be connected to a local electronic device 220, and the local electronic device 220 can have the same components that were described with reference to FIG. 3 and FIG. 4. The local electronic device 220 shown in FIG. 5 could be connected to a remote electronic device (250 in FIG. 3 or FIG. 4) using either a wired or a wireless connection as was described with reference to FIG. 3 and FIG. 4. The embodiment shown in FIG. 5 can also include an external device or vehicle as was shown with reference to FIG. 3 and FIG. 4.

Figure 6:
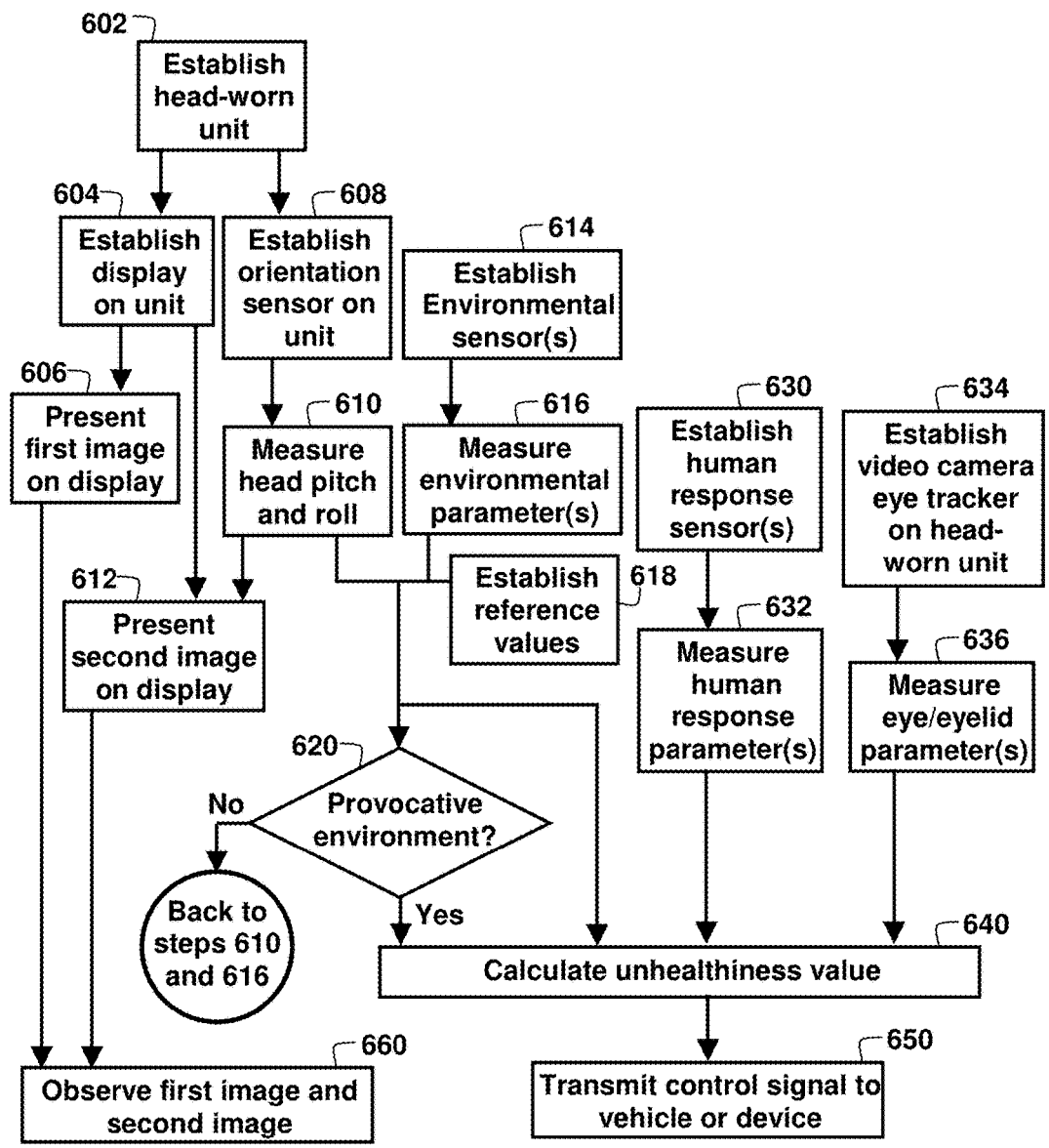
FIG. 6 illustrates a method for controlling a vehicle or device in response to measured unhealthy human response to a provocative environment.

FIG. 6 illustrates a method for controlling a vehicle or device in response to a measured unhealthy human response to a provocative environment. In one embodiment, the method begins by establishing a head-worn unit, shown at step 602. In this embodiment, the head worn unit has a display (established in step 604) and an orientation sensor (established in step 608) and may have an eye tracker camera (established in step 634). In this embodiment, a first image is displayed (step 606), and the first image is not responsive to pitch and roll of the head-worn unit. The orientation sensor from step 608 is used in step 610 to measure head pitch and roll, which in turn is used in step 612 to present a second image on the display, wherein the second image is sensitive to the measured pitch and roll from step 610. In the embodiment of the method shown in FIG. 6, there are one or more environmental sensors, a step shown at 614. Just like in the description for FIG. 3 and FIG. 4, the environmental sensor or sensors can be of any type and placed in any location presented in this disclosure and capable of being understood by anyone skilled in the art. The environmental sensor or sensors are used to measure environmental parameters as shown in step 616. Reference values for head pitch, head roll, and any environmental parameters are also established as shown in step 618. The measured head pitch and roll (from step 610), the measured environmental parameters (from step 616, and the reference values (from step 618) are then compared in step 620 to determine if the environment is provocative. If it is determined that the environment is not provocative, the method continues by measuring head pitch and roll (step 610) and measuring environmental parameters (step 616) until such time that the environment is determined to be provocative (step 620).

The method shown in FIG. 6 includes using one or more established human response sensors, as shown in step 630. The human response sensors can be located in any suitable place and be of any appropriate type as was discussed with reference to FIG. 3 and FIG. 4 and in other parts of this disclosure. The human response sensors are used to measure human response parameters, as shown at step 632. The method can also use one or more video cameras that operate as eye tracker(s), or eyelid tracker(s), on the head-worn unit as shown in step 634. The eye/eyelid tracker(s) can measure eye and/or eyelid parameters as shown in step 636. The eye or eyelid parameters that are measured in step 636 can be any parameters described in other parts of this disclosure or that are capable of being understood by anyone skilled in the art.

The determination of whether the environment is provocative (from step 620), the measured head pitch and roll (from step 610), the measured environmental parameters (from step 616), the reference values (from step 618) the measured human response parameters (from step 632), and the measured eye and/or eyelid parameters (from step 636) can all be put into an algorithm (shown at step 640) that calculates an unhealthiness value and this unhealthiness value can then be used to transmit a control signal to a vehicle or device as shown at step 650. Additionally, in the step shown at 660, the person wearing the head-worn unit can look at the display to see both the first image (from step 606) and the second image (from step 612), and use this comparison to help mitigate unhealthiness symptoms from a provocative environment.

An algorithm can be used to calculate an unhealthiness value (step 640 in FIG. 6). Sensors (such as those shown at

132, 134 and 136 in FIG. 3, FIG. 4, and FIG. 5) and the eye camera video processor (224 in FIG. 3, FIG. 4 and FIG. 5) can measure physical human health parameters and transmit this information to the central processing unit (232 in FIG. 3, FIG. 4 and FIG. 5). The algorithm can be responsive to one or more health parameters. As an example, the indicators of an abnormal physical response that could trigger the transmission of a control signal to a vehicle or device (step 650 in FIG. 6) could include:

a. The presence of nystagmus with nystagmus velocity greater than 12 degrees per second, sustained over at least 1 minute
b. Galvanic response of greater than 5K ohms, indicating a high level of brain arousal (tense level) sustained over at least 3 minutes
c. Detection of Delta waves (frequency waves up to 4 Hz) with EEG measurements
d. Detection sleep spindles and K complexes with Theta waves (frequency waves 4.5-6 Hz) with EEG measurements
e. Blood pressure (systolic) greater than 200 mmHg or less than 80 mmHg or Diastolic greater than 120 mmHg
f. Heart rate less than 50 beats per minute or greater than 200 beats per minute, sustained over at least 10 minutes
g. Respiratory rate of less than 10 per minute or greater than 30 per minute, sustained over at least 5 minutes
h. Blood oxygen saturation of less than 85%
i. Body or skin temperature of greater than 104 degrees (F.) or less than 97 degrees (F.)
j. Blood Ph of less than 7.35 or greater than 7.5
k. Glucose levels less than 70 milligrams per deciliter or greater than 250 milligrams per deciliter
l. Blood alcohol greater than 0.04 percent
m. Lowering of the upper eyelid for at least 60 seconds, with the upper eyelid less than 2 mm from mid-pupil, indicating fatigability.
n. Eye lid blink rate that last for at least 5 seconds with a slowed blink rate of less than 10 per 30 seconds The indicators of an abnormal physical response could be combined with indicators that determine whether the environment is provocative. Examples of indicators for whether the environment is provocative could include:

a. Inverted position greater than 30 seconds;
b. Air pressure, indicative of 12,000 ft altitude; and/or
c. Atmospheric carbon dioxide level greater than 2,000 parts per million.

Algorithm embodiments can also include the following:

a. The eye camera can measure retinal scans, corneal reflections, pupillary reflections, and/or reflections from the iris. If the camera and/or camera video processor detects eye lid findings suggestive of sleepiness or if the eye findings detect inattentiveness such as reading reflected text information, as from a smart phone or similar device, the abnormal data can be electronically interfaced with the operational controller system of a vehicle or powered equipment to identify that the driver is inattentive.
b. The unhealthiness value 640 can elicit a pre-programmed response. These abnormal values can also be sent, in real time, to a remote source to notify the remote location of the status of the operator. Additionally, the operator can receive an alarm, which can be auditory, visual, or haptic. Even normal physiology-based biometrics including voice as "voice command controllers" can trigger the controller that can then, as with the abnormal eye movements, control the vehicle or powered equipment.
c. If abnormal eye movements are detected by the eye tracker, the symbology suite can become visible, if it was not visible previously. If the symbology is present in the visual field and abnormal eye movement (e.g. saccades or nystagmus) becomes evident or occurs, the symbology can become more brightly visible to enable the user to focus more on the technology to mitigate the symptoms of motion sickness, disorientation and dizziness. The colors of the symbology suite can vary as well as the shape.

Figure 7:
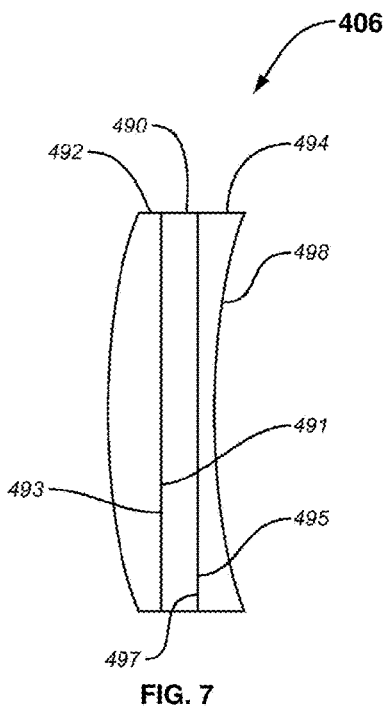
FIG. 7 illustrates an embodiment of a display region.

FIG. 7 illustrates an embodiment of a display region 406. This is the same as display regions 406 and 408 in FIG. 2 and FIG. 5. This display region may be different in a VR, AR, MD, or synthetic environment, but the same technologies and principles may be applied. The display region 406 contains central components 490 and outer lenses, 492 and 494. The central components 490 are digital displays. A myriad of display technologies can be used in the digital displays 490, examples of which include but are not limited to light emitting diode (LED), organic light emitting diode (OLED), Flexible OLEDs and liquid crystal on silicon (LCOS) and wave guide array technologies or other displays such as low temperature Poly Silicon (LTPS) and excimer laser annealing (ELA) displays. Different applications may call for different choices of display technology. The factors to consider are the pixel size, the lumen output, the efficiency or power required to achieve the desired lumen output. For avionics requiring daytime usage a higher light output is necessary. Therefore, for such an embodiment the applicants found an arrayed waveguide display (AWD) to be particularly suitable to obtain a suitable lumen output with adequate resolution in an eyeglass mounted display.

The outer lenses 492 and 494 can be combined to create the desired focal plane for the display. In one embodiment, the desired focal length for the display is approximately two to three feet or about a meter. In other embodiments, other focal lengths can be used up to infinity (focal lengths of about fifteen to twenty (15-20) feet and beyond serve as effectively infinity for the human eye). It is preferred that the mating surfaces 493, 491 and 497, 495 match to reduce the internal reflect between the components and so that if desired the components can be adhered/glued together to further reduce internal reflections within and between the components. The embodiment illustrated in FIG. 9 employs flat mating surfaces 493, 491, 497, 495. This has been found to allow for relatively thin lenses. In this embodiment of a lens set it is possible to account for user specific vision correction by shaping the user facing surface 498 to the inside lens 494. In alternative embodiments, other shaped mating surfaces may be employed. In further embodiments, the display may be manufactured in a substrate that is thick enough to be ground so that the lens set is comprised of a single lens. In further embodiments, it might be desirable to include thin film coatings on the lenses that would optimize their use in particular conditions such as night vision, in daylight or prescription requirements.

Symbology.

Alternate embodiments of the symbology are shown in FIG. 8A to FIG. 17B. The choice of symbology is of critical importance to success of any system or method to mitigate the unhealthy effects of a provocative motion environment. Experience has shown that successful use of display symbology depends on both the type of information presented and how this information is provided. The symbology described herein has been demonstrated to be successful. Many factors can be important to the success of the cue symbology including shape(s), color(s), refresh rate for presenting the symbology, and dynamic mechanization(s) of the symbology. The particular combinations of symbology and symbology elements and functions may vary based on application and individual. For example, symbology optimized to treat medical issues, is likely to be different from symbology appropriate to healthy individuals in a motion-provocative aviation environment, which is likely to be different than symbology needed in an immersive VR, AR, MD, or synthetic environment. With even more granularity, different symbology may be appropriate for two different medical conditions. Similarly, different symbology may be appropriate for different military applications such as driving a jet fighter, flying a drone remotely, or driving a tank. Nevertheless, some features may be common, such as the use of a head attitude scale (HAS), a pitch roll indicator (PRI), and a head-rotation/yaw indicator (Hill).

Head-Attitude Scale (HAS).

Figure 8A:
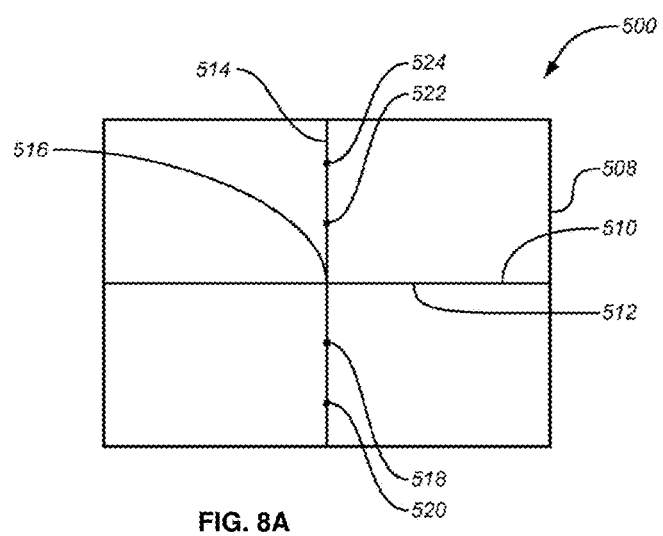
FIG. 8A to FIG. 8I illustrate display symbology that can be used with embodiments of the present invention, in which, more specifically.

For purposes of this disclosure and the appended claims, a head-attitude scale (HAS) can be defined as an image that is fixed to a head-worn display and therefore does not move in a user's field of view (FOV) when the orientation of the user's head changes. Referring to FIG. 8A, a head-worn display is shown at 500. A field of view (FOV), shown at 508, is the rectangle that surrounds the other elements and the HAS 510 comprises the elements inside of the FOV 508. In some embodiments, the HAS 510 is a magenta-colored Cartesian grid with equal-length x (horizontal) axis 512 and y (vertical) axis 514 lines that intersect in their respective centers at the origin (vertex) 516. In some embodiments the HAS 510 is centered in, and extends to the limits of, the display FOV 508 as depicted in FIG. 8A. In the embodiment shown in FIG. 8A, the horizontal axis 512 represents a range of plus or minus 180 degrees of lateral rotation (yaw) from the vertex 516 and has no graduations (or indices). The vertical axis 514 presents a range of plus or minus ninety degrees of up-down vertical rotation (pitch) and has four short indices 518, 522 and 520, 524 respectively representing plus or minus forty-five degrees and plus or minus ninety degrees pitch displacement from the vertex 516. In this embodiment, the vertical axis 514 extends past the useable scale plus or minus ninety degrees 524 and 520 in order to provide continued visual stimulation and stability in the vertical plane to the limits of the FOV 508. No symbols are displayed above or below the plus or minus ninety degrees indices on the HAS horizontal axis 512 or vertical axis 514.

Pitch/Roll Indicator (PRI).

Figure 8B:
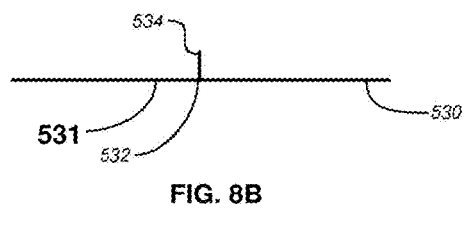
Figure 8C:
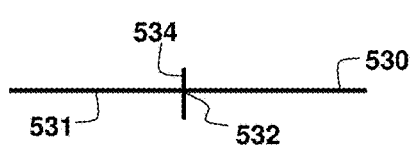

For purposes of this disclosure and the appended claims, a pitch roll indicator (PRI) can be defined as an image that changes position, orientation, color, and/or shape as a result of changes in pitch and/or changes in roll of a user's head. In some embodiments shown in this disclosure, the PRI can be combined with an HAS in a head-worn display to provide the wearer of the display with a visual comparison of his/her orientation relative to an artificial horizon. Referring to FIG. 8B, an embodiment of a Pitch/Roll Indicator (PRI) is illustrated at 530. In some embodiments, the PRI 530 can be a tangerine-colored line with a length approximately one-third the length of the HAS horizontal axis (512 in FIG. 8A). In other embodiments, such as the one shown in FIG. 8B, the PRI can be approximately the same length as the horizontal span of the user's FOV. In the embodiment shown in FIG. 8B, the PRI 530 can be comprised of two perpendicular lines 531 and 534 with the shorter of the two lines 534 placed on top and in the center 532 of the longer line 531. The longer PRI line 531 can also be called the pitch/roll bar. The shorter PRI line can also be called the vertical fin.

Figure 8D:
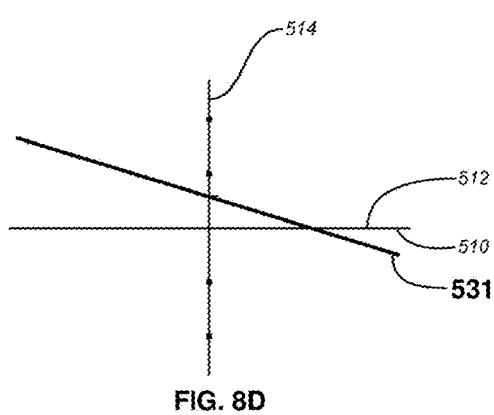

FIG. 8D illustrates a very simple PRI superimposed on a HAS 510. The PRI in FIG. 8D consists only of the pitch/roll bar 531. The pitch/roll bar 531 can be a tangerine-colored line with approximately the same length as the horizontal span of the user's FOV. The pitch/roll bar can move vertically up and down and can rotate (tilt) about the vertical axis 514 of the HAS 510 in response to changes in head orientation for a user of the head-worn unit that incorporates the display. Consequently, the position and orientation of the pitch/roll bar 531 represents the pitch and roll attitude of the user's head relative to the real-world horizon as presented by the HAS 510. Pitch can be shown as changes in the intersection between the pitch/roll bar and the vertical (Y) axis 514 and can be measured by comparison with the graduations on the Y-axis. Roll can be shown as a rotation of the pitch/roll bar relative the HAS 510. The relative position and orientation of the pitch/roll bar in FIG. 8D can be interpreted to represent a pitch upward of approximately 30 degrees and a roll rightwards of approximately 18 degrees.

Figure 8E:
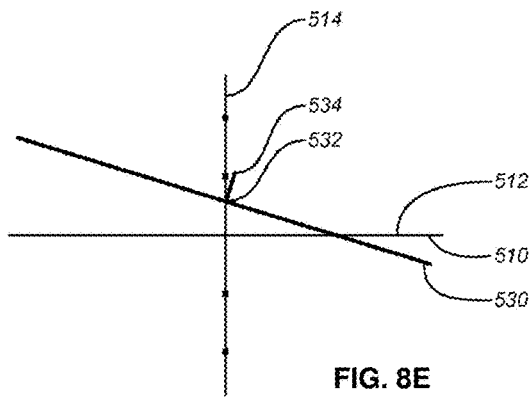

FIG. 8E illustrates the PRI 530 of FIG. 8B superimposed on the same HAS 510 that was shown in FIG. 8A and FIG. 8D. In this illustration, the shorter line (vertical fin) 534 presents the direction toward the top of the user's head and can be considered to point in the direction of the lift vector of an aircraft when the wearer is sitting upright in the seat. In this embodiment, the vertical fin's 534 height is approximately one-ninth the length of pitch/roll bar. In this embodiment the PRI 530 can be tangerine-colored when roll attitude is less than or equal to plus or minus ninety degrees as referenced to the HAS horizontal 510 and vertical axis 514 and red colored when roll attitude is greater than plus or minus ninety degrees.

In the embodiments illustrated in FIG. 8A, FIG. 8B, FIG. 8C, FIG. 8D, and FIG. 8E, the PRI 530 is an "outside-in" presentation and represents the wearer's head position as if viewed from a distance from (or outside) the head. For example, head tilt to the right can be presented as a right-tilted pitch/roll bar 531 in relation to the vertical axis 514 of the HAS 510 (i.e. the vertical fin 534 "points" to the right of the vertical axis 514). Similarly, an upward tilt of the head can be displayed by positioning the pitch/roll bar 531 on the positive side of the HAS horizontal 510 scale relative to the vertical axis 514 as illustrated in both FIG. 8D and FIG. 8E. In both FIG. 8D and FIG. 8E, the pitch/roll bar 531 rotation is conformal to the real-world (outside scene) in roll, but not in pitch. For example, 18 degrees of rotation to the right can be displayed as 18 degrees of roll, while PRI elevation (climb) and depression (dive) are compressed. In other embodiments, the angular range of view may differ, as may the compression ratio. In yet other embodiments, the compression ratio may not be linear. In both models the PRI is limited vertically when it reaches the plus or minus ninety degree index on the HAS. Some embodiments rotate up to 180 degrees, while the other embodiments may rotate 360 degrees.

Head-Rotation/Yaw Indicator (HRI).

Figure 8F:
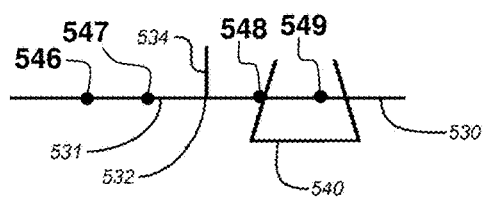

An embodiment of a Head-Rotation/Yaw Indicator 540 is illustrated in FIG. 8F as an open-ended, three-sided trapezoid. If this was presented in color, the HRI 540 might be tangerine-colored. As illustrated in FIG. 8F, the HRI 540 "slides" the length of the pitch/roll bar 531, as the user's head is rotated left or right of straight ahead about the central axis of the user's head. In the embodiment illustrated, the HRI 540 extends above and below the pitch/roll bar 531, but its height is less than the height of the vertical fin 534. The center of the HRI 540 trapezoid remains coincident with the center of the pitch/roll bar 531 during pitch changes, while it moves independently along the pitch/roll bar 531 when the wearer's head position changes in lateral rotation. The lateral position of the HRI 540 remains constant as long as the wearer's head is rotated away from straight ahead in relation to his or her body. In alternative embodiments, the HRI 540 can also represent the rotational position of the—user's head relative to his trunk. In avionics applications, this latter embodiment has proven to be more effective for some users. Also shown in FIG. 8F are graduations (or indices) at 546, 547, 548, and 549 on the pitch/roll bar 531. The pitch/roll bar graduations (546, 547, 548, and 549) can allow the user to more accurately estimate the number or degrees of yaw being shown by the HRI 540. These pitch/roll bar graduations are optional, which is why they are shown in some embodiments, and not in others. In the embodiment show, each tic (or index or graduation) represents 45 degrees of yaw.

Figure 8G:
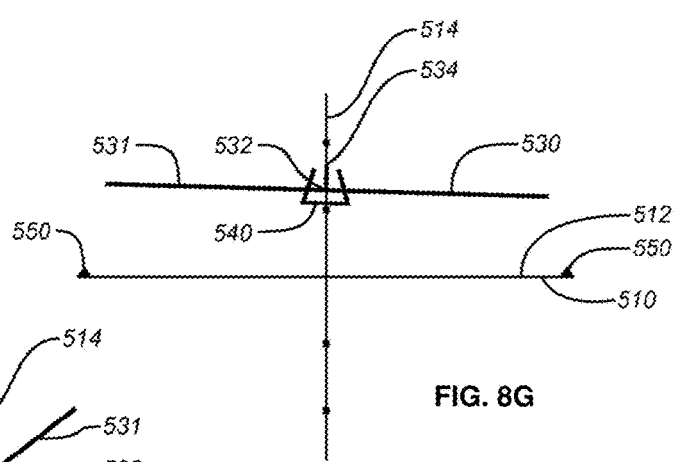

FIG. 8G illustrates an embodiment of a Head-Rotation/Yaw Indicator (HRI) in conjunction with a Pitch Roll Indicator (PRI), with both the HRI and the PRI being superimposed on the user's field of view (FOV). In this embodiment, the pitch can be approximately 50 degrees above the horizontal as illustrated by the Y-intercept of the PRI 530 on the HAS vertical line 514. The roll can be approximately zero degrees because the PRI roll bar 531 is approximately parallel with the horizontal axis 512. There is also no Yaw because the HRI 540 is approximately centered on the vertical axis 514.

Upright/Inverted (UI) Triangles.

Figure 8H:
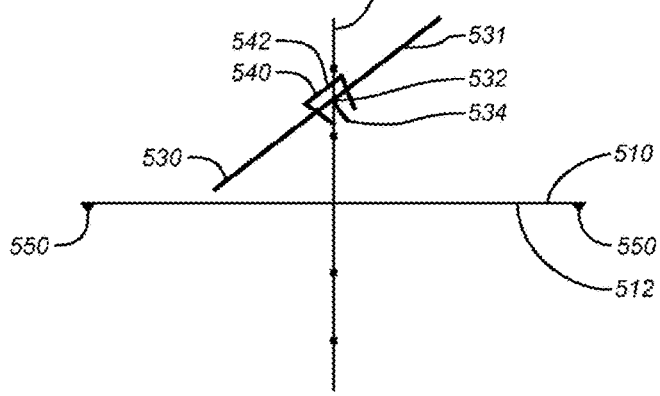
Figure 8I:
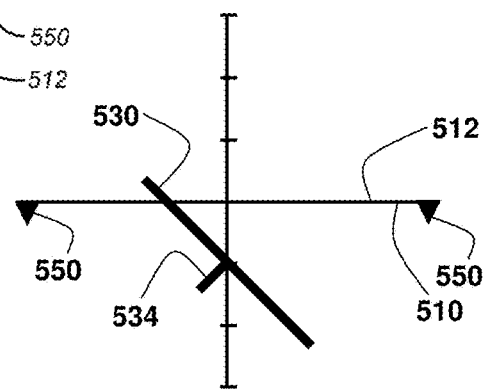

FIG. 8G also shows triangles 550 at the ends of the HAS horizontal axis 512. These triangles are upright/inverted indicators (UI) and are labeled at 550. In one embodiment, the UI triangles 550 can be green in color, and the apexes point upward, when the user is upright, as determined by the PRI 530 indicating less than or equal to ±90 degrees of roll as referenced to the HAS 510 horizontal axis 514. When roll is greater than ±90 degrees, the triangles can change color to red, and the apexes point downward, indicating inverted as shown in FIG. 8H. Thus, FIG. 8H shows that the person is inverted, has a pitch of about 65 degrees upward, no yaw, and an "upside down" roll of about 135 degrees to the right (or 45 degrees from being perfectly inverted. The embodiment in FIG. 8I is similar to the embodiment in FIG. 8H, but has no HRI. In the embodiment in FIG. 8I, the person's head is inverted, has a pitch of about 45 degrees downward and an upside down roll of about 135 degrees to the left (or 45 degrees from being perfectly inverted).

Focal Length.

As previously described, the preferred embodiment the display of the symbology suite focused at a range of approximately two (2) feet in contrast to 15 feet/infinity. Testing revealed this focal length can make the symbology more effective in controlling spatial disorientation/motion sickness (SD/MS) and provided a recognizable contrast in symbology from the flight control and fire control targeting symbology associated with HMD (helmet mounted display) and HUD (heads up display) embodiments.

Colors. The colors cited above were selected based on a particular avionics application.

The colors were selected both for their visibility and so that they do not conflict with other symbology presented to the user by other avionics subsystems such as a targeting system. In other applications, other colors may be desirable. For example, for systems employed for particular use in the dark such as nighttime, it may be desirable to use green colors in order to maintain night vision. In further embodiments, the focal lengths may vary with the symbology. For example, some symbology may be displayed at different focal lengths than other symbology.

Offset Vs. Bore Sight Display.

In some embodiments, the location of the symbology within the field of view can be programmable. For example, the location of the symbology may be offset from the center bore sight to allow the user to better see through the display and to enhance compatibility with other optical displays such as HMD or night vision equipment and symbology such as fire control targeting symbology. In one embodiment the symbology is presented off bore sight up 10-15 degrees and left about 30-45 degrees to one side or the other (preferably to the left for the left eye or to the right for the right eye. When the symbology can be displayed off bore sight, can shrink to fit. In some embodiments, the symbology can still however be set on bore-sight taking the same view-space of his other instruments if desired by the user.

In further embodiments, the symbology can remain off bore sight during normal operation. However, if the avionics sensors experiencing triggering events that suggest that the pilot has begun to experience or may begin to experience spatial disorientation, the symbology can increase in size as it moves from off bore sight to on bore sight. In such events, other parameters of the symbology may also be enhanced such as the thickness and color or color intensity. In some embodiments, the enhancement may be escalated as the indications of spatial disorientation increase for potential to actual to loss of control. In some embodiments, as the situation escalates, other symbology presented to the user may be overridden to give the user a chance to reorient with out the disorienting stimulation of the other symbology. For example, if the pilot is experiencing nystagmus the fire control targeting symbology may be removed in favor of the reorientation symbology described herein. In further embodiments, the user can be provided with the option to declutter or deescalate the enhancement of the symbology presentation to the user.

Monocular Versus Binocular Embodiments

Embodiments of the system and method described herein could be implemented using a single display (monocular), viewable by either one eye or by both eyes. An avionics subsystem with a monocular display has been shown to be effective in controlling SD/MS while reducing power requirements and the amount of-visual clutter in front of a user's eyes. A single display embodiment can allow for reduced pixilation and computational requirements enhancing reliability and miniaturization. Embodiments of the system and method could also be implemented using two displays (binocular), where each display is visible by one eye. In binocular embodiments, the two displays could show: (a) the identical view of the identical scene, (b) the identical scene with slightly different views to give a stereoscopic effect, or (c) two scenes and/or symbologies that are not identical. VR, AR, MD, and synthetic environments can be implemented using binocular displays with stereoscopic views that "immerse" the user into the scene. The symbology can similarly be stereoscopic and immersive when using a binocular display. Regarding the eye and/or eyelid sensors, there can be embodiments with a sensor (or sensors) to look at only one eye (and/or eyelid), or there could be separate sensors for each eye (and/or eyelid).

Variable Symbology.

When using the system or method, the user could have the choice of selecting what can be displayed, where it can be displayed in the field of view, and when it can be displayed. This can depend on the environment, it can depend on the application of the system, and/or it can depend on the application of the system or method. For example, in a VR, AR, MD or synthetic environment, the user could have the option to control what is visualized with the symbology and how it is displayed by only displaying a horizontal line, displaying a horizontal line and the pitch and roll indicator, or clearly displaying pitch, roll, and yaw. Any one of the reference symbologies discussed previously can be used in any combination, based on what is most effective. The symbology may also be displayed only when the user is experiencing motion-related symptoms. The symbology may be displayed in anticipation of motion-related symptoms. The symbology can be displayed at all times. The symbology can be automatically adjusted (e.g. brighter or dimmer, center bore situated or off bore), depending on the tracked responses of the eye movements, or they can be manually adjusted.

Figure 9A:
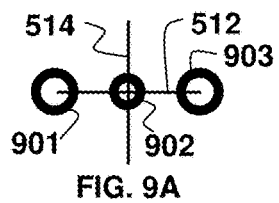
Figure 9B:
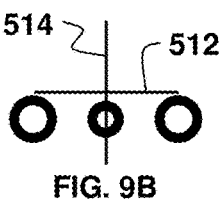
Figure 9C:
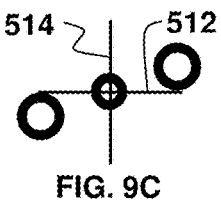
Figure 9D:
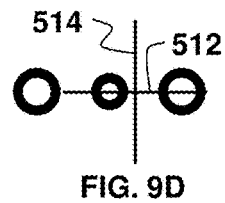

FIG. 9A through FIG. 16D illustrate further embodiments of combinations of head attitude scale (HAS) horizontal axes 512 and HAS vertical axes 514 in combination with pitch/roll indicators (PRIs) and head-rotation/yaw indicators (HRIs). FIG. 9A, FIG. 9B, FIG. 9C, and FIG. 9D show a display symbology in which the PRI is three circles, shown at 901, 902, and 903, in a line. FIG. 9A shows the PRI centered. FIG. 9B shows pitch down. FIG. 9C shows roll to the left. FIG. 9D shows yaw to the left.

Figure 10A:
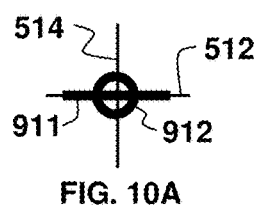
FIG. 10A, FIG. 10B, FIG. 10C, and FIG. 10D show a display symbology in which the Pitch Roll Indicator can be a horizontal line with a circle in the center in a centered, pitch down, roll left, and yaw left view, respectively.
Figure 10B:
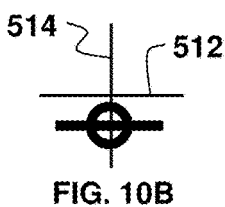
Figure 10C:
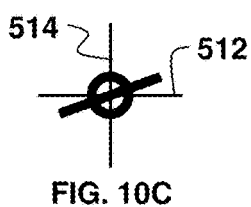
Figure 10D:
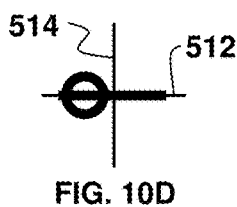

FIG. 10A, FIG. 10B, FIG. 10C, and FIG. 10D show a display symbology in which the PRI is a line 911 with a circle in the center 912. FIG. 10A shows the PRI centered. FIG. 10B shows pitch down. FIG. 10C shows roll to the left. FIG. 10D shows yaw to the left.

Figure 11A:
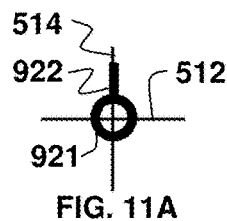
FIG. 11A, FIG. 11B, FIG. 11C, and FIG. 11D show a display symbology in which the Pitch Roll Indicator can be a circle with a vertical line in a centered, pitch down, roll left, and yaw left view, respectively.
Figure 11B:
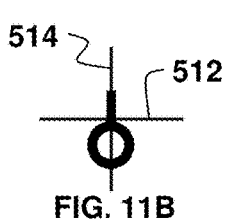
Figure 11C:
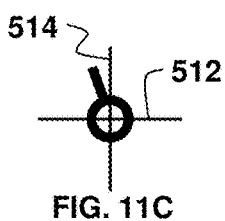
Figure 11D:
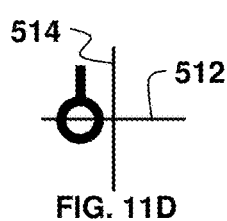

FIG. 11A, FIG. 11B, FIG. 11C, and FIG. 11D show a display symbology in which the PRI is a circle 921 with a vertical line 922. FIG. 11A shows the PRI centered. FIG. 11B shows pitch down. FIG. 11C shows roll to the left. FIG. 11D shows yaw to the left.

Figure 12A:
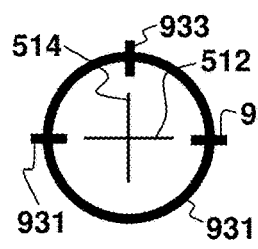
FIG. 12A, FIG. 12B, FIG. 12C, and FIG. 12D show a display symbology in which the Pitch Roll Indicator can be a large circle with line segments at the 9 o'clock, 12 o'clock, and 3 o'clock positions in a centered, pitch down, roll left, and yaw left view, respectively.
Figure 12B:
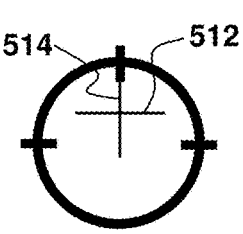
Figure 12C:
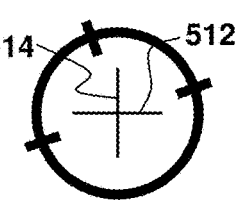
Figure 12D:
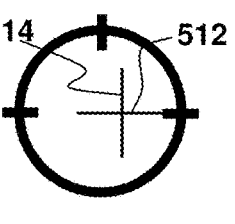

FIG. 12A, FIG. 12B, FIG. 12C, and FIG. 12D show a display symbology in which the PRI is a large circle 931 with line segments at the 9 o'clock 932, 12 o'clock 933, and 3 o'clock 934 positions. FIG. 12A shows the PRI centered. FIG. 12B shows pitch down. FIG. 12C shows roll to the left. FIG. 12D shows yaw to the left.

FIG. 13A, FIG. 13B, FIG. 13C, and FIG. 13D show a display symbology in which the PRI is a horizontal ellipse, shown at 941. FIG. 13A shows the PRI centered. FIG. 13B shows pitch down. FIG. 13C shows roll to the left. FIG. 13D shows yaw to the left.

FIG. 14A, FIG. 14B, FIG. 14C, and FIG. 14D show a display symbology in which the PRI is a horizontal ellipse 951 and a solid circle 952. FIG. 14A shows the PRI centered. FIG. 14B shows pitch down. FIG. 14C shows roll to the left. FIG. 14D shows yaw to the left.

FIG. 15A, FIG. 15B, FIG. 15C, and FIG. 15D show a display symbology in which the PRI is a horizontal line 961 and two triangles, shown at 962 and 963. FIG. 15A shows the PRI centered. FIG. 15B shows pitch down. FIG. 15C shows roll to the left. FIG. 15D shows yaw to the left.

FIG. 16A, FIG. 16B, FIG. 16C, and FIG. 16D show a display symbology in which the PRI is a half ellipse 971 and three line segments, shown at 972, 973, and 974. FIG. 16A shows the PRI centered. FIG. 16B shows pitch down. FIG. 16C shows roll to the left. FIG. 16D shows yaw to the left.

Figure 17A:
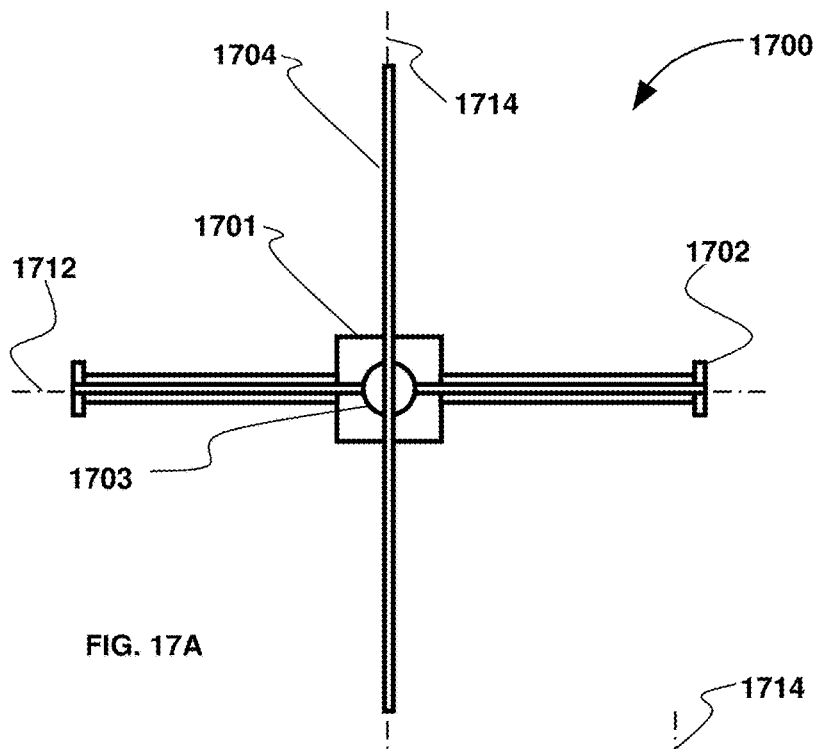
FIG. 17A and FIG. 17B show an alternate embodiment of the symbology in which the orientation of the user is presented as a virtual gimbal.
Figure 17B:
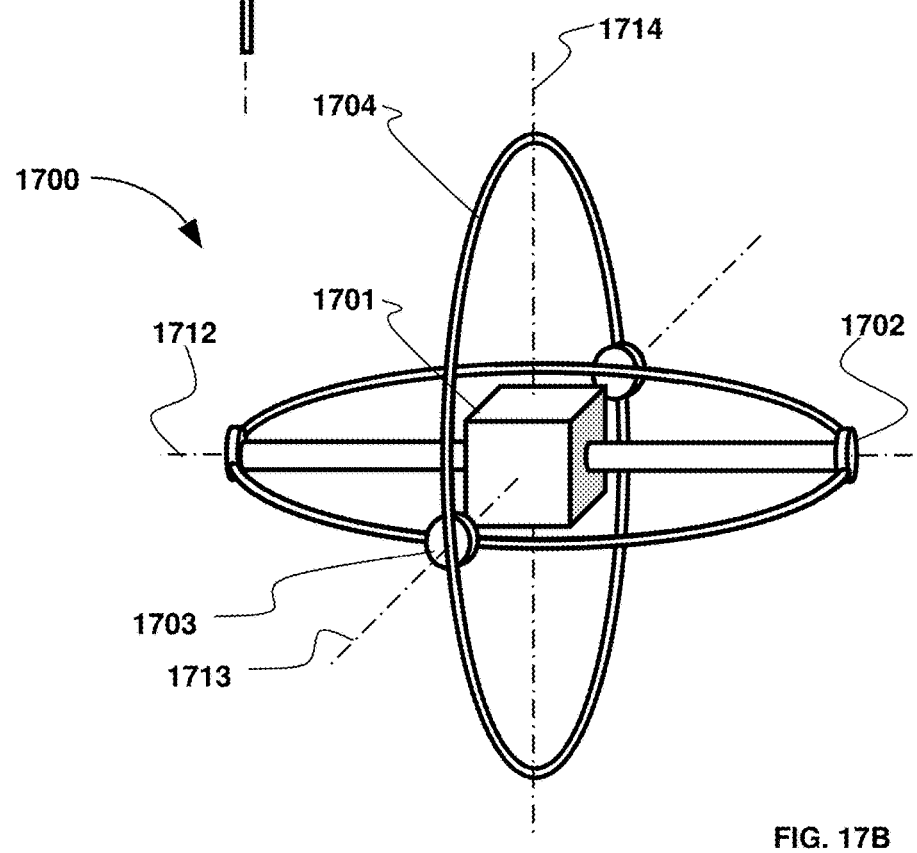

In the embodiments of the symbology shown so far, the PRI is typically shown as a two-dimensional object and the user must synthesize its meaning based on instruments or visual analogs that might look similar. FIG. 17A and FIG. 17B show an example of an embodiment of three-dimensional symbology in the form of a virtual gimbal 1700 in which pitch, roll, and yaw can be presented in a perspective view with the location of the pivots and the rotation of the pivots providing visual cues. In FIG. 17A, the user is in a neutral orientation (i.e. pitch=0, roll=0, and yaw=0), which means that the user is looking straight at the cube at the center. In FIG. 17B, there is pitch downward and yaw to the left. Referring to FIG. 17A and FIG. 17B, an inner object is shown at 1701. In the embodiment shown, the inner object 1701 is a cube. The inner object 1701 could be any other shape, but an unmarked sphere would not be recommended because an unmarked sphere would not provide any information about orientation. If it were a sphere with markings on it, such as one with a globe, it could provide orientation cues. The markings on the inner stable object could be of any type capable of being understood by anyone skilled in the art, and could use symbols, shading, colors, shapes, patterns, etc. The user is stable around this moving object in an "outside in" view that can be more clearly understood by observing the orientation of the yaw plane (outer ring) 1704, the roll pivots 1703, and the pitch pivots 1702. This can also be understood by looking at the yaw axis 1714, the roll axis 1713, and the pitch axis 1712.

Other types of symbology can include:
(a) An embodiment in which the PRI may not be seen to be in contact with the HAS.
(b) The symbology for the axes can comprise text data.
(c) The symbology can include auditory signals
(d) An embodiment displaying only the artificial horizon and the center point of fixation can be visualized and this artificial horizontal line and center vertex region may be symbolized as a line or other linear object or form appearing horizontally and having a central point of fixation.
(e) The axes could resemble see through bubbles, which represent movement in each axis. These axes can be represented by multiple bubbles immersive in their motion in the plane of axial rotation of the head. In this embodiment, as the head pitches forward the superior vertical bubble appears smaller and the inferior vertical bubble can appear to be larger. The bubble tilts left with rolling the head left and as the head rotates left the left bubble appears larger and the rightward balloon appears smaller. The artificial horizon and point of fixation can be located in the center of the bubble axis or axes, or it can be positioned in another location, unconnected to axes of rotation. The bubbles or axis that they represent can be visualized as active and immersive objects moving in space, representing the head or body orientation in space. As rotation occurs the length of the axis can change (e.g. when bending forward (e.g. anterior pitch of the head) the axis which the bubble is attached appears smaller.
(f) Only one bubble could be visible and its rotation can represent movement of the user's movement in the plane of the axial rotation of the user's head or body. The artificial horizon and point of fixation can be located within an immersive bubble.

The colors, forms and shapes of the symbology may have a number of variations and be adaptable based on the environment, the user's symptoms, and the application.

Use of Embodiments in a VR, AR, MD, and/or Synthetic Environment

In embodiments of the present invention, the artificial horizon (HAS line or horizontal aspect of the virtual horizon) can be seen as remaining horizontal in order for the user to focus on this aspect when experiencing motion sickness in these above noted environments. As more severe symptoms occur, the user would focus on the more center aspect (vertex) of the artificial horizontal line to control the vertigo or severe motion sickness.

Exposure to VR, AR, MD and synthetic display environments has revealed that several adverse health effects can be induced by viewing motion images, including visual fatigue (also termed asthenopia), or eyestrain, vection induced motion sickness and VIMS. Symptoms of visual fatigue induced by images comprise eye discomfort and tiredness, pain and sore around the eyes, dry or watery eyes, headaches and visual distortions such as blurred and double visions, and difficult in focusing. The main physiological mechanism involved with the onset of visual fatigue concerns the intense eye accommodation activity of 3D movie viewers, such as focusing and converging. Eye focus cues (accommodation and blur in the retinal image) target the depth of the display (or of the movie screen) instead of the displayed scene, generating unnatural depth perception. Additionally, uncoupling between vergence and accommodation affects the binocular fusion of the image. Both processes may generate visual fatigue in susceptible individuals.

The specific disturbance deriving from viewing 3D movies has been named "3D vision syndrome" but the relative occurrence of different symptoms in spectators and the individual characteristics that make some individuals more susceptible than others still remain to be described. Occurrence of self-reported symptoms in young healthy adults during or immediately after watching a 3D movie may be high, although often quickly disappearing once they finished viewing. Factors reported to be associated with VIMS can be categorized into factors associated with the visual stimuli provided to viewers, factors associated with the position from where the viewers are watching the movie and the psychophysiological conditions of the viewers. Examples include (but are not limited to): the characteristics of the (moving) images (e.g. the optic flow) such as the earth axis along which the visual field is made rotating, the amplitude of the field of view, the display angle, the feeling of immersion or presence, the co-presence of vection, the display types, postural instability, habituation, age, gender, and anxiety levels of viewers. Interactions and additive effects among factors may also be present, making difficult to predict the final outcome (if a given individual will or will not suffer VIMS).

Despite this incessant retinal motion, images are perceived as static and clear. The visual system has mechanisms to deal with movement and the eventual blur resultant from the retinal image slip caused by fixation of eye movements. These mechanisms fail when the amount of movement is above their capacity of neutralization. In these conditions, the image is perceived as blurred due to motion smear. An immediate consequence of blur is a diminution of resolution. Gaze control in various conditions is important, since retinal slip deteriorates the perception of 3-D shape of visual stimuli. The finding that VIMS is associated with inappropriate eye movements is consistent with the findings that suppression of eye movements by fixation can significantly reduce levels of VIMS. Afferent signals in the ocular muscles will trigger vagal nuclei, resulting in a range of sickness symptoms associated with the autonomous nervous systems—the nystagmus theory. Because eye movements follow foveal stimulation and vection follows peripheral stimulation, the nystagmus theory indicates that in the presence of foveal stimulation, sickness will correlate with eye movements but not necessarily with vection. In a prior study using an Optokinetic drum with this invention, it was seen that both vection scores and simulator sickness scores were statistically significantly lower when the invented symbology was visualized, compared to when the technology was not visually apparent to the user.

Introducing fixation into stimulated or a VR, AR, MD and synthetic environments reduce the foveal slip and motion sickness and prevents image fading in central vision. However, in the periphery a higher amount of movement is necessary to prevent this fading. The effects of increased retinal image slip are different for simple (non-crowded) and more complex (crowded) visual tasks. Prior results provide further evidence for the importance of fixation stability on complex visual tasks when using the peripheral retina. Embodiments of this invention can prevent both foveal slip and peripheral retinal slip velocity.

Mismatches can be caused where there are differences in stimuli as processed by the brain. Mismatches can occur where there is motion, or where there is no motion. These mismatches may be caused by delays in the delivery or processing of the stimuli or mismatch of stimuli even without delay. Examples of mismatches are seen in persons suffering from vertigo or persons in a virtual space such as a video game or flight simulator or targeting system. A solution is needed in VR, AR, MD, and synthetic platforms that will enable a person to participate in such activities where visual scene motion does not evoke illusory self-motion or motion sickness and participate in motion provocative activities without having motion sickness, spatial disorientation, vertigo and loss of human performance activities. Such an improvement in the application of VR, AR, MD, or synthetic environments can be used for mitigating, preventing or controlling symptoms of motion sickness, simulation sickness, gaming sickness, spatial disorientation, dizziness, 3-D vision syndrome or vision induced motion sickness.

Embodiments of the present invention can be used in a head worn immersive VR, AR, MD, and synthetic visual display devices and can provide symbology such as an artificial horizon and 3 axial orientation with 6 degrees of freedom to provide visual orientation to the user about the user's position in space. As described in this disclosure, embodiments of the present invention can be comprised of different symbology seen within a head worn VR, AR, MD, and synthetic environment device and provides a method for orientation to mitigate or prevent motion sickness. Embodiments of the present invention can be used in many fields, including but not limited to: sports, entertainment, film, medicine, military, social, gaming, simulator and other vocational and commercial applications for training, education or rehabilitation purpose. Embodiments of the present invention, utilized in these fields can comprise an eye tracker and or head tracker for eye movement analysis. This eye tracker measurement and analysis can observe abnormal eye movements and eye reflexes, which can be used for diagnosis of a particular health abnormality or be used to predict athletic or other vocational-health performance. Another embodiment used in a VR, AR, MD or synthetic environment can include abnormal physiologic measurements for determining various health aspects of the user. In other embodiments, sensors attached to the worn device, can be in contact with the skin of the user and measure health status can be displayed to the user or remotely transmitted and the device can be controlled.

7. USING THE MEASURED UNHEALTHY RESPONSE

The measured unhealthy response to a provocative environment can be used by the system and method for a variety of purposes, examples of which are listed below.

(a) Medical rehabilitation. Embodiments of this invention within an immersive virtual platform can be used for balance and vertigo rehabilitation. In the rehabilitation environment, a balance disorder due to inner ear pathology, central nervous system pathology or musculoskeletal pathology can be treated with the visualized symbology displayed to user in an immersive virtual platform to correct the balance abnormality. If there is an associated abnormality of eye movement or eye reflexes (such as nystagmus or abnormal saccades), this can be measured, with the use of the eye tracker and head tracker, and treated with rehabilitation. During the therapy process, other physiologic parameters can be measured; such as vital signs and other physiologic levels. If parameters are measured from a post-traumatic disorder, such as high cortisol, the user can be desensitized or the threshold of sensitivity can be altered in the rehabilitation environment. The rehabilitation process can help the user combat the anticipated experiences in the future to prevent recurrence. If an eye movement abnormality is found with head movement, while using the invention in a VR or AR environment, the eye abnormality can be identified and a rehabilitation program can be designed to correct the abnormality. The symbology to mitigate motion disorders can enable the affected person to visualize and remain engaged in the immersive environment for as long a time as necessary to receive the necessary benefits of re-conditioning. Embodiments of the invention can be used in the same immersive virtual platforms for vestibular rehabilitation, cognitive evaluation, cognitive rehabilitation, and psycho/social rehabilitation. The loss of proprioception with injuries to extremities can result in loss of balance. Embodiments of the present invention, when used in a VR, AR, MD, or synthetic environment, can shortened rehabilitation and recovery times for the user by giving them orientation information as well as preventing them from having motion sickness, dizziness and disorientation and enabling them to use the virtual platform for a greater length of time during the rehabilitation.

(b) Medical diagnosis of abnormalities. Any person with a motion sensitivity disorder (such as motion sickness, vection induced motion sickness, or visually induced motion sickness) or a balance problem, either of a visual or peripheral origin, may experience an abnormality of eye movement, such as nystagmus, abnormal saccades or an abnormality of the eye response with movement. Individuals with such an abnormality will express symptoms of dizziness, disorientation, difficulty with focusing, nausea, fuzziness, and such other complaints as not being clear headed. They may also other physical responses that can be measured. The physical abnormalities measured can be used in an algorithm to generate a control signal. Example indicators could be seen measuring the eyelid response from an operator of a vehicle, or any other device who has consumed drugs or alcohol, or is operating the equipment when drowsy or inattentive and the eyelids demonstrate a prolonged blink rate or has an abnormally high measured amount of blood alcohol. Both have measured physical responses that can be used to trigger a response to generate a control signal to the vehicle or device. Head trauma can have some measurable EEG responses that can be used to trigger an algorithm to generate a control signal to the vehicle or device.

(c) Performance measurement. If there is decay in human performance, while operating a device, due to harmful physiologic changes, the abnormal measured changes can provide an alarm and control the device in order to prevent an adverse event and record physiological parameters for later analysis.

(d) Education and training. Eye tracking can be used to monitor the abnormal eye movements of persons in simulator training. The equipment can reveal whether trainees are scanning gauges in the right sequence, or skipping one altogether. Similarly, embodiments of the invention could be used for driver training, in either a physical or a virtual environment. Embodiments of the invention can be used for education and training in medicine and surgery, for example training student personnel in a virtual hospital, while mitigating motion sickness, dizziness and disorientation.

(e) Entertainment and gaming. It is common for persons to experience motion sickness or disorientation while watching movies in immersive VR, AR, MD, and synthetic environments. Similarly watching movement, such as with flying, sky diving, driving, vehicular motion, or action visual displays can be provocative and can result in motion-induced symptoms. Embodiments of the present invention mitigate motion-related symptoms in these environments, by viewing the user orientation symbology and vertex with artificial horizon. In addition, different types of stereoscopic display viewing or stroboscopic viewing can induce eye symptoms and cause sickness symptoms. Embodiments of the present invention can reduce visual fatigue, visual discomfort, and other visual symptoms in these situations. Embodiments the present invention can not only control the symptoms of motion sickness, but can also track abnormal physical responses in these types of situations. When individuals communicate with others and share immersive experiences, such as travel, moving in vehicles, moving in crowds and the like in a VR, AR, MD, or synthetic environment, symptoms of motion sickness and disorientation will occur. Embodiments of the invention can prevent or mitigate the symptoms and allow the user to more easily participate in the social media virtual experience. This suppression of motion-provoked responses, by visualizing the symbology, can be generalized to include any kind of display involving motion, including viewing sporting events, viewing movies, viewing games.

(f) Sports performance. Embodiments of the present invention can be used by people watching immersive virtual sport activities in which accurate visual cues might be lacking or insufficient. Embodiments of the present invention can be used by people observing physical sports activities that are visually provocative such as observing sailing, soccer, contact sports, flying, auto racing and the like. In these environments, observers can experience a loss of situation awareness, disorientation and motion sickness.

(g) Commercial. Embodiments of the present invention can also be used in other industries where individuals are operating vehicles, controllers, computers, computer interfaces, and other devices. Industries which use VR, AR, MD, and synthetic environments, such as space planning, architecture, photography, urban planning, real estate, film making, engineering projects and the like can have motion sickness, visual induced motion sickness or dizziness. Embodiments disclosed herein can prevent or mitigate these symptoms and enable the user to continue use of the systems for the designed use. Embodiments can be used for shopping and other immersive activity.

A number of variations and modifications of the disclosed embodiments can also be used. The principles described here can also be used for other applications than sports, entertainment, film, medicine, military, social, gaming, simulator and other vocational and commercial applications for training, education or rehabilitation purpose. While the principles of the disclosure have been described above in connection with specific apparatuses and methods, it is to be clearly understood that this description is made only by way of example and not as limitation on the scope of the disclosure.

I claim:

1. A system comprising:
   a head-attachable unit configured for attachment to a head of a person wherein the head-attachable unit further comprises:
      an orientation sensing element responsive to a pitch of the person's head and a roll of the person's head wherein the head pitch represents a rotation about a first axis representing up and down movement of a face of the person while a rear of the person's head moves in the opposite direction and the head roll represents rotation about a second axis perpendicular to the head pitch axis in which a face of the person rotates about a nose of the person when looked at from a front of the person;
      a control circuit, wherein the control circuit produces an orientation sensor signal responsive to the orientation sensing element; and
      a head-attachable display viewable by the person wherein the head-attachable display comprises:
         a first image that is not responsive to pitch of the person's head and not responsive to roll of the person's head; and
         a display element viewable by the person wherein the display element is responsive to the orientation sensor signal and the display element comprises a virtual gimbal;
   a first human response sensor wherein the first response sensor comprises a sensor selected from the group of a galvanic skin response sensor; a blood pressure sensor, and an electroencephalograph;
   a second human response sensor wherein the second response sensor comprises a video camera wherein the video camera is responsive to an eye parameter selected from the group of a palpebral movement, nystagmus, and a saccade;
   a third human response sensor wherein the third response sensor is responsive to the person's heart rate;
   a physical response detection algorithm, wherein:
      the algorithm is computed in a digital processor responsive to the orientation sensing element, the first human response sensor, the second human response sensor; and
      the heart rate sensor; and
      the algorithm computes a human physical condition signal that measures a condition selected from the group of dizziness, vertigo, motion sickness, motion intolerance, and spatial disorientation; and
   an electronic interface configured for transmitting the human physical condition signal to an external system selected from the group of a vehicle and a device.

2. The system of claim 1 wherein:
   the system comprises a fourth human response sensor wherein the fourth response sensor is responsive to a blood oxygen saturation of the person and the algorithm is responsive to the blood oxygen saturation; and
   the display comprises a first display screen viewable by the person's left eye and a second display screen viewable by the person's right eye; wherein:
      the display element is viewable on the first display screen and the second display screen; and
      the display element comprises a stereoscopic display element.

3. The system of claim 1 wherein:
   the head-attachable unit is a helmet;
   the first image comprises a vertical line and a horizontal line;
   the first human response sensor is a galvanic skin response sensor;
   the system comprises a fourth human response sensor wherein the fourth response sensor is responsive to a blood oxygen saturation of the person and the algorithm is responsive to the blood oxygen saturation;
   the system comprises a fifth human response sensor wherein the fifth response sensor is responsive to an expired respiratory blood oxygen level of the person and the algorithm is responsive to the expired respiratory oxygen level;
   the system comprises a sixth human response sensor wherein the sixth response sensor is responsive to an expired respiratory carbon dioxide level of the person and the algorithm is responsive to the expired respiratory carbon dioxide level;
   the system comprises a seventh human response sensor wherein the seventh response sensor is responsive to a respiratory rate of the person and the algorithm is responsive to the respiratory rate;
   the system comprises an eighth human response sensor wherein the eighth response sensor is responsive to a blood glucose level of the person and the algorithm is responsive to the blood glucose level;
   the system comprises a ninth human response sensor wherein the ninth response sensor is responsive to a blood sodium level of the person and the algorithm is responsive to the blood sodium level;
   the system comprises a tenth human response sensor wherein the tenth response sensor is responsive to a blood hemoglobin level of the person and the algorithm is responsive to the blood hemoglobin level;
   the system comprises an eleventh human response sensor wherein the eleventh response sensor is responsive to a blood alcohol level of the person and the algorithm is responsive to the blood alcohol level;
   the system comprises a twelfth human response sensor wherein the twelfth response sensor is responsive to a blood lactate level of the person and the algorithm is responsive to the blood lactate level;
   the system comprises a thirteenth human response sensor wherein the thirteenth response sensor is responsive to an electroencephalograph of the person and the algorithm is responsive to the electroencephalograph;
   the system comprises a fourteenth human response sensor wherein the fourteenth response sensor is responsive to an electrocardiogram of the person and the algorithm is responsive to the electrocardiogram;
the system comprises a fifteenth human response sensor wherein the fifteenth response sensor is responsive to a body temperature of the person and the algorithm is responsive to the body temperature;
the system comprises a first environmental input sensor wherein the first environmental input sensor is responsive to an air pressure and the algorithm is responsive to the air pressure;
the system comprises a second environmental input sensor wherein the second environmental input sensor is responsive to an oxygen level and the algorithm is responsive to the oxygen level;
the electronic interface transmits the human physical condition to an aircraft; and
the system comprises an auditory alarm responsive to the algorithm.

4. The system of claim 1 wherein:
the system is configured for controlling a vehicle.

5. A system comprising:
a unit attachable to a person's head wherein the head-attachable unit comprises:
an orientation sensing element responsive to pitch of the head and roll of the head;
a control circuit, wherein the control circuit produces an orientation sensor signal responsive to the orientation sensing element; and
a head-attachable display viewable by the person wherein the head-attachable display comprises:
a first image that is not responsive to pitch of the head and not responsive to roll of the head; and
a second image viewable by the person wherein:
the second image is responsive to the orientation sensor signal; and
the second image comprises a virtual gimbal;
a first human response sensor wherein the first response sensor comprises a sensor selected from the group of a galvanic skin response sensor; a blood pressure sensor, and an electroencephalograph;
a physical response detection algorithm, wherein:
the algorithm computes a human physical condition signal in response to the orientation sensing element and the first response sensor; and
the human physical condition signal is a measure of a condition selected from the group of dizziness, vertigo, motion sickness, motion intolerance, and spatial disorientation; and
an electronic interface configured for transmitting the human physical condition signal.

6. The system of claim 5 wherein:
the first image comprises a first left image and a first right image;
the first left image is different from the first right image;
the first left image comprises a moving computer generated visual element viewable by the person's left eye;
the first right image comprises a moving computer generated visual element viewable by the person's right eye; and
a combination of the first left image and the first right image create a three-dimensional visual environment selected from the group of a virtual reality environment, an augmented reality environment, and a synthetic environment; and
the second image is responsive to the first human response sensor.

7. The system of claim 5 wherein:
the system comprises a second human response sensor wherein the second response sensor comprises a video camera wherein the video camera is responsive to an ocular movement selected from the group of nystagmus and a saccade; and
the algorithm is responsive to the ocular movement.

8. The system of claim 7 wherein:
the second human response sensor is responsive to vection nystagmus detected as a temporal involuntary eye movement caused by self-perceived motion sensation as a result of a physiological effect selected from the group of vertigo, motion sickness, motion intolerance, and spatial disorientation resulting from sensory mismatch between the person's visual, vestibular, and proprioceptive organs.

9. The system of claim 7 wherein:
the second human response sensor is responsive to a saccade detected as a quick simultaneous movement of a left eye and a right eye in the same direction indicative of a physiological effect selected from the group of sleepiness, vertigo, motion sickness, motion intolerance, and spatial disorientation.

10. The system of claim 5 wherein:
the system comprises a second human response sensor wherein the second response sensor comprises a video camera wherein the video camera is responsive to a palpebral movement; and
the algorithm is responsive to the palpebral movement.

11. The system of claim 5 wherein:
the first human response sensor comprises a galvanic skin response sensor; and
the algorithm is responsive to the galvanic skin response sensor.

12. The system of claim 5 wherein:
the first human response sensor comprises a blood pressure sensor; and
the algorithm is responsive to the blood pressure sensor.

13. The system of claim 5 wherein:
the first human response sensor comprises an electroencephalograph; and
the algorithm is responsive to the electroencephalograph.

14. The system of claim 5 wherein:
the system further comprises a heart rate sensor; and
the algorithm is responsive to the heart rate sensor.

15. The system of claim 5 wherein:
the display is opaque;
the display comprises a first display screen viewable by the person's left eye and a second display screen viewable by the person's right eye and a stereoscopic image;
the first human response sensor comprises a galvanic skin response sensor;
the system further comprises a second human response sensor wherein the second response sensor comprises a video camera wherein the video camera is responsive to an eye parameter selected from the group of a palpebral movement, nystagmus, and a saccade;
the system further comprises a heart rate sensor;
the system further comprises a respiratory rate sensor;
the system further comprises a blood alcohol sensor;
the system further comprises an electroencephalograph; and
the algorithm is responsive to the video camera, the heart rate sensor, the respiratory rate sensor, the blood alcohol sensor, and the electroencephalograph.

16. The system of claim 5 wherein:
the system is configured for controlling a vehicle.

17. A system comprising:
a unit attachable to a person's head wherein the head-attachable unit comprises:
- an orientation sensing element responsive to orientation of the person's head;
- a control circuit, wherein the control circuit produces an orientation sensor signal responsive to the orientation sensing element; and
- a head-attachable display viewable by the person wherein the head-attachable display comprises:
  - a first display element not responsive to orientation of the person's head; and
  - a second display element responsive to the orientation sensing element wherein the second display element comprises a virtual gimbal;

a first human response sensor wherein the first response sensor is configured for measuring a human response selected from the group of a skin response; a blood pressure, a heart signal; and a brain signal;

a physical response detection algorithm, wherein:
- the algorithm computes a human physical condition signal in response to the orientation sensing element and the first response sensor; and
- the human physical condition signal is a measure of a condition selected from the group of dizziness, vertigo, motion sickness, motion intolerance, and spatial disorientation.

* * * * *